(12) United States Patent
Sasanuma et al.

(10) Patent No.: US 7,665,347 B2
(45) Date of Patent: Feb. 23, 2010

(54) LIQUID STATE DETECTING APPARATUS

(75) Inventors: Takeo Sasanuma, Niwa-gun (JP); Yoshikuni Sato, Nagoya (JP)

(73) Assignee: NGK Spark Plug Co., Ltd., Aichi (JP)

( * ) Notice: Subject to any disclaimer, the term of this patent is extended or adjusted under 35 U.S.C. 154(b) by 251 days.

(21) Appl. No.: 11/594,887

(22) Filed: Nov. 9, 2006

(65) Prior Publication Data

US 2007/0113625 A1    May 24, 2007

(30) Foreign Application Priority Data

Nov. 11, 2005    (JP) .......................... P2005-328198

(51) Int. Cl.
*G01N 25/00* (2006.01)
(52) U.S. Cl. .................................... 73/61.46
(58) Field of Classification Search ............... 73/53.01, 73/61.41, 61.46, 25.05, 304 R, 204.26, 861.01, 73/861.04, 861.08, 200.5, 291, 114.71, 114.75, 73/54.42; 60/286; 204/400, 403.01, 409; 205/775, 789.5
See application file for complete search history.

(56) References Cited

U.S. PATENT DOCUMENTS

| | | | | |
|---|---|---|---|---|
| 4,909,225 A | * | 3/1990 | Gonze et al. ................. | 123/494 |
| 5,182,942 A | * | 2/1993 | Hartel et al. ................ | 73/61.46 |
| 5,604,441 A | * | 2/1997 | Freese et al. ................. | 324/663 |
| 7,377,185 B2 | * | 5/2008 | Kawanishi et al. ........ | 73/861.95 |
| 2004/0060344 A1 | * | 4/2004 | Kauffman et al. .......... | 73/53.01 |
| 2004/0251919 A1 | * | 12/2004 | Stahlmann et al. .......... | 324/663 |
| 2007/0006639 A1 | * | 1/2007 | Sasanuma et al. .......... | 73/53.01 |
| 2007/0113625 A1 | * | 5/2007 | Sasanuma et al. .......... | 73/61.46 |
| 2008/0087009 A1 | * | 4/2008 | Nishina et al. ................ | 60/301 |
| 2008/0110158 A1 | * | 5/2008 | Esaka .......................... | 60/286 |
| 2008/0289399 A1 | * | 11/2008 | Cooper et al. .............. | 73/53.01 |

FOREIGN PATENT DOCUMENTS

| | | | |
|---|---|---|---|
| EP | 1669743 A1 | * | 6/2006 |
| WO | WO 2006/067900 A1 | | 6/2006 |

* cited by examiner

*Primary Examiner*—John Fitzgerald
(74) *Attorney, Agent, or Firm*—Sughrue Mion, PLLC

(57) ABSTRACT

A liquid state detecting apparatus including a detecting element which outputs a signal associated with a concentration of a particular component of a liquid contained in a liquid container; an abnormality determination unit which determines whether or not the liquid is in a particular abnormal state based on the output signal of the detecting element, a level detecting part which outputs a signal according to a level of the liquid contained in the liquid container; and a static state determination unit which determines whether or not the liquid in the liquid container is in a static state based on the output signal from the level detecting part, wherein the determination made by the static state determination unit is reflected in the determination made by the abnormality determination unit.

8 Claims, 15 Drawing Sheets

LIQUID STATE DETECTING APPARATUS

BACKGROUND OF THE INVENTION

1. Field of the Invention

The present invention relates to a liquid state detecting apparatus for detecting the concentration and level of a liquid contained in a liquid container.

2. Description of the Related Art

Recently, a catalyst for selective catalytic reduction (SCR) of NOx is sometimes used in an exhaust gas cleaner for reducing nitrogen oxide (NOx) exhausted, for example, from a diesel automobile into a harmless gas, and an aqueous urea solution is used as the reducing agent. It is known that the use of an aqueous urea solution having a urea concentration of 32.5% by weight allows for efficient reduction. However, the urea concentration of an aqueous urea solution contained in a urea-water tank carried by an automobile may change as time passes. Further, a foreign liquid or water may be introduced into a urea-water tank by mistake. Under these circumstances, in order to allow control over the urea concentration of the aqueous urea solution, the concentration is detected by mounting a concentration sensor for detecting the urea concentration in the urea-water tank.

It is known that the thermal conductivity of an aqueous urea solution varies depending on its concentration. Under these circumstances, a concentration sensor having two temperature sensing bodies (sensor elements) having a resistance which changes with the temperature disposed thereon in parallel is mounted in the urea-water tank, and one of the temperature sensing bodies is heated by energizing the same. The conduction of heat to the other temperature sensing body is affected by the concentration of the aqueous urea solution, and the urea concentration of the aqueous urea solution can therefore be detected based on the difference between on the measured resistance values of the two bodies (for example, see Japanese Patent No. 3686672). When the detected urea concentration is outside a certain range, abnormalities can be detected including a determination that a foreign liquid or water is included in the urea-water tank and a determination that no aqueous urea solution is present.

When a diesel automobile is driven, the aqueous urea solution contained in the urea-water tank may be agitated or shaken by the vibration of the vehicle body. In the case of the concentration sensor of Japanese Patent No. 3686672, urea concentration detected by the same may be read as a value that is greatly different from what it should be. This can occur when the resistance values of the sensor elements become disproportionate to the urea concentration as a result of agitation or shaking of the aqueous urea solution which can cause irregularities in the concentration of the aqueous urea solution or remove beat from the sensor elements. For this reason, according to Japanese Patent No. 3686672, whether or not the aqueous urea solution is in a static state is determined based on the driving state of the diesel automobile (specifically, the vehicle speed). If the liquid is not in a static state, it is assumed that there is a possibility of erroneous detection, and the determination of an abnormality in concentration is made using a different weighting from that used in a static state.

3. Problems to be Solved be the Invention

However, according to Japanese Patent No. 3686672, the speed of the diesel automobile is used to indirectly indicate whether an aqueous urea solution in a urea-water tank is in a static state. Since this indirect indication may differ from the actual agitation state of the aqueous urea solution, a problem has arisen in that an abnormality in concentration may not be accurately determined.

The invention was made to solve the above-described problems, and it is an object of the invention to provide a liquid state detecting apparatus which can more accurately identify an abnormality in concentration by determining the static state of a liquid contained in a liquid container based on liquid level.

SUMMARY OF THE INVENTION

The above-described object of the invention has been achieved by providing a liquid state detecting apparatus (inventive embodiment 1) comprising a detecting element which outputs a signal associated with the concentration of a particular component of a liquid contained in a liquid container, and an abnormality determination unit which determines whether or not the liquid is in an abnormal state based on the output signal of the detecting element. The apparatus is also characterized in that it comprises a level detecting part which outputs a signal according to the level of the liquid contained in the liquid container and a static state determination unit which determines whether or not the liquid in the liquid container is in a static state based on the output signal of the level detecting part, wherein the determination made by the static state determination unit is reflected in the determination made by the abnormality determination unit.

In addition to inventive embodiment 1, the liquid state detecting apparatus of the invention according to an inventive embodiment 2 comprises an abnormality detecting unit which tentatively detects whether or not the liquid is in an abnormal state based on the output signal of the detecting element and a threshold set in association with the abnormal state, a counter unit which increments an abnormality determination value by a predetermined count value each time the abnormality determination unit determines that the liquid is in the particular abnormal state, and a set value changing unit which sets at least one of the predetermined count value and an abnormality determination value seeing as a reference for the determination made by the abnormality determination unit to a first value when the static state determination unit determines that the liquid is in a static state and to a different value when the liquid is not in the static state. The apparatus is also characterized in that the abnormality determination unit determines that the liquid is in the particular abnormal state when the abnormality count value incremented by the counter unit reaches the abnormality determination value. Also, the result of the determination by the static state determination unit is reflected in the determination made by the abnormality determination unit by the change in the setting of at least one of the predetermined count value and the abnormality determination value made by the set value changing unit.

In addition to inventive embodiments 1 and 2, the liquid state detecting apparatus of the invention according to an inventive embodiment 3 is characterized in that it comprises a level signal storing unit which acquires the signal from the level detecting part twice or a greater number of times within a predetermined period and in which at least a maximum value and a minimum value of the signals from the level detecting part within the predetermined period are stored. The apparatus is also characterized in that the static state determination unit determines that the liquid is not in a static state when a level difference that is the difference between the maximum value and the minimum value of the signals from the level detecting part stored in the level signal storage unit is greater than a reference level difference serving as a reference for determining the static state.

In addition to the inventive embodiments 2 and 3, the liquid state detecting apparatus of the invention according to an inventive embodiment 4 is characterized in that the detecting element includes a heating resistor which generates heat when energized and a concentration detecting unit which obtains the value of a difference between a first corresponding value corresponding to a first resistance of the heating resistor acquired after energization of the heating resistor is started and a second corresponding value corresponding to a second resistance acquired after the heating resistor is energized for a certain period of time and which detects the concentration of a particular component included in the liquid associated with the difference. The apparatus is also characterized in that the abnormality detecting unit compares at least one of the difference and the concentration with a threshold set in association with the particular abnormal state of the liquid to detect whether or not the liquid is in the particular abnormal state.

In addition to any one of inventive embodiments 1 to 4, the liquid state detecting apparatus of the invention according to an inventive embodiment 5 is characterized in that the level detecting part includes a first electrode and a second electrode extending in the longitudinal direction thereof to form a capacitor whose electrostatic capacity changes according to the level of the liquid contained in the liquid container between the first electrode and the second electrode. The apparatus is also characterized in that the detecting element is integrated with the level detecting part in an insulated state with a part of the detecting element itself located beyond a tip of the level detecting part.

In addition to any one of inventive embodiments 1 to 5, the liquid state detecting apparatus of the invention according to an inventive embodiment 6 is characterized in that it comprises a notification unit which notifies an external circuit that the liquid is in the particular abnormal state when so determined by the abnormality determination unit.

In addition to any one of inventive embodiments 1 to 6, the liquid state detecting apparatus of the invention according to an inventive embodiment 7 is characterized in that the particular abnormal slate of the liquid is any of a state in which liquid is not present in the liquid container, a state in which a foreign liquid is included in the liquid container, or a state in which the concentration of the particular component included in the liquid is regarded as being abnormal.

In addition to any one of inventive embodiments 1 to 7, the liquid state detecting apparatus of the invention according to an inventive embodiment 8 is characterized in that the liquid is an aqueous urea solution and in that the particular component is urea.

The liquid state detecting apparatus of the invention according to inventive embodiment 1 determines whether a liquid in a liquid container is in a static state based on a signal from a level detecting part which can detect the level of the liquid. According to the invention, since agitation of the liquid in the liquid container can be directly detected from fluctuations in the level of the same, the static state of the liquid can be determined more accurately. The result of the determination of the static state is reflected in at least either a predetermined count value or an abnormality determination value, and the detection of an abnormal state of a liquid can therefore be weighted based on whether or not the liquid is found to be in a static state. For example, assume that a liquid is not in a static state such that there is a rapid flow of the liquid around a detecting element. Then, a great difference can temporarily occur between a signal associated with the concentration of a particular component in the liquid and a value reflecting the actual concentration of the particular component, which can result in an erroneous determination that an abnormal state has occurred. If the result of determination of a static state is reflected in a process of determining an abnormal state as described above, it is possible to prevent an incorrect determination of the occurrence of an abnormal state from being immediately made.

As a method of reflecting the result of determination of a static state in the process thus described, as disclosed in inventive embodiment 2, a liquid may be determined to be in a particular abnormal state only when the particular abnormal state of the liquid is detected a plural number of times. Thus, the number of opportunities for detecting the abnormal state (e.g., the number of times the detection is conducted) in the process of determining when the liquid is not in a static state can be made greater than the number of opportunities for detecting the abnormal state when the liquid is in a static state. Alternatively, the determination of the particular abnormal state may be interrupted when it is determined that the liquid is not in a static state, and the detection of the particular abnormal state may be resumed when a static state is restored, which may be implemented in combination with the above-described method. The determination of an abnormal state of a liquid can be performed with improved reliability when the determination of the abnormal state is weighted based on whether or not the liquid is in a static state by reflecting the result of determination of the static state in at least either a predetermined count value or an abnormality determination value.

Referring to the determination of a static state of a liquid, as disclosed in inventive embodiment 3, a difference between a maximum value and a minimum value of a signal from the level detecting part acquired twice or a greater number of times within a predetermined period or a difference between liquid levels attributable to upward and downward movements of the liquid may be compared with a reference level difference serving as a reference. Thus, an accurate determination can be made as to whether the liquid is in a static state in the liquid container or whether the liquid is agitated such that the liquid level can fluctuate.

Since the thermal conductivity of a liquid depends on the concentration of a particular component included in the liquid, liquids having different concentrations undergo a temperature rise at different rates when the liquids are heated for a certain period of time using a heating resistor. According to the invention set forth in inventive embodiment 4, a heating resistor is energized for a certain period of time, and the degree of temperature rise at the heating resistor can be obtained based on the value of a difference between a first corresponding value corresponding to a first resistance taken after the energization of the heating resistor is started and a second corresponding value corresponding to a second resistance taken after the heating resistor is energized for a certain period of time, which makes it possible to detect the concentration of a particular component included in a liquid. Whether or not the liquid is in a particular abnormal state can be detected by comparing at least either the difference obtained in detecting the concentration or the detected concentration itself with a threshold set in association with the particular abnormal state of the liquid.

The first corresponding value may be any kind of value as long as it corresponds to the first resistance of the heating resistor. Specifically, it may be a voltage, a current, a temperature obtained by converting the resistance, or the like. The second corresponding value may also be any kind of value as long as it corresponds to the second resistance of the heating resistor. In the case of inventive embodiment 4 in which the value of a difference between the second corresponding value and the first corresponding value must be obtained, when the first corresponding value is, for example, a voltage, the second corresponding value must also be a voltage.

Referring to timing for acquiring the first corresponding value in the invention according to inventive embodiment 4, the value may be acquired within a period following the start of the energization of the heating resistor in which the temperature of the heating resistor itself is substantially the same as the temperature of the liquid surrounding the same. Specifically, the first corresponding value may be acquired within 100 msec after the start of energization of the heating resistor. Since there is a tendency that the current supplied to the heating resistor is not easily stabilized at the start of energization of the heating resistor, the first corresponding value is preferably acquired in a period starting when 2 msec have elapsed after the start of energization of the heating resistor and ending within 100 msec (more preferably within 50 msec) after the start of energization.

According to the invention set forth in the inventive embodiment 5, the level detecting part for determining the presence of a static state and the detecting element for detecting the concentration of the liquid are integrated while being insulated from one another. In such a configuration, the volume occupied by the liquid state detecting apparatus in the liquid container can be made relatively small when compared to the volume occupied by a device for detecting the level of a liquid and a device for detecting the concentration of the liquid separately disposed in the liquid container. This makes it possible to increase the maximum amount of the liquid that can be contained in the liquid container. Further, since a mounting part for mounting the liquid state detecting apparatus in a liquid container can be disposed only in one location, air-tightness and water-tightness can be maintained between the liquid container and the mounting part with a simple configuration. Since at least part of the detecting element is located beyond the tip of the level detecting part facing in the direction in which the level of a liquid decreases, the element can be kept immersed in the liquid for a somewhat prolonged period even when the level of the liquid decreases, which allows for stable detection of the concentration of the liquid.

The liquid state detecting apparatus of the invention according to inventive embodiment 6 can notify an external circuit of an abnormality only when the liquid is determined to be in a particular abnormal state. Specifically, even if a temporary abnormal state of the liquid is detected in the apparatus, a particular abnormal state of the liquid is not determined to have occurred unless the abnormal state continues. Therefore, an external circuit can be notified of an abnormal state with high reliability.

As disclosed in the invention according to inventive embodiment 7, the particular abnormal state of a liquid may be any of a state in which the liquid is not present in the liquid container, a state in which the liquid container includes a foreign liquid, and a state in which a particular component included in the liquid has an abnormal concentration.

The liquid state detecting apparatus of the invention according to inventive embodiment 8 can accurately detect and determine a particular abnormal state of an aqueous urea solution by outputting a signal associated with the concentration of urea included in the aqueous urea solution from the detecting element.

DESCRIPTION OF REFERENCE NUMERALS

Figure 1:
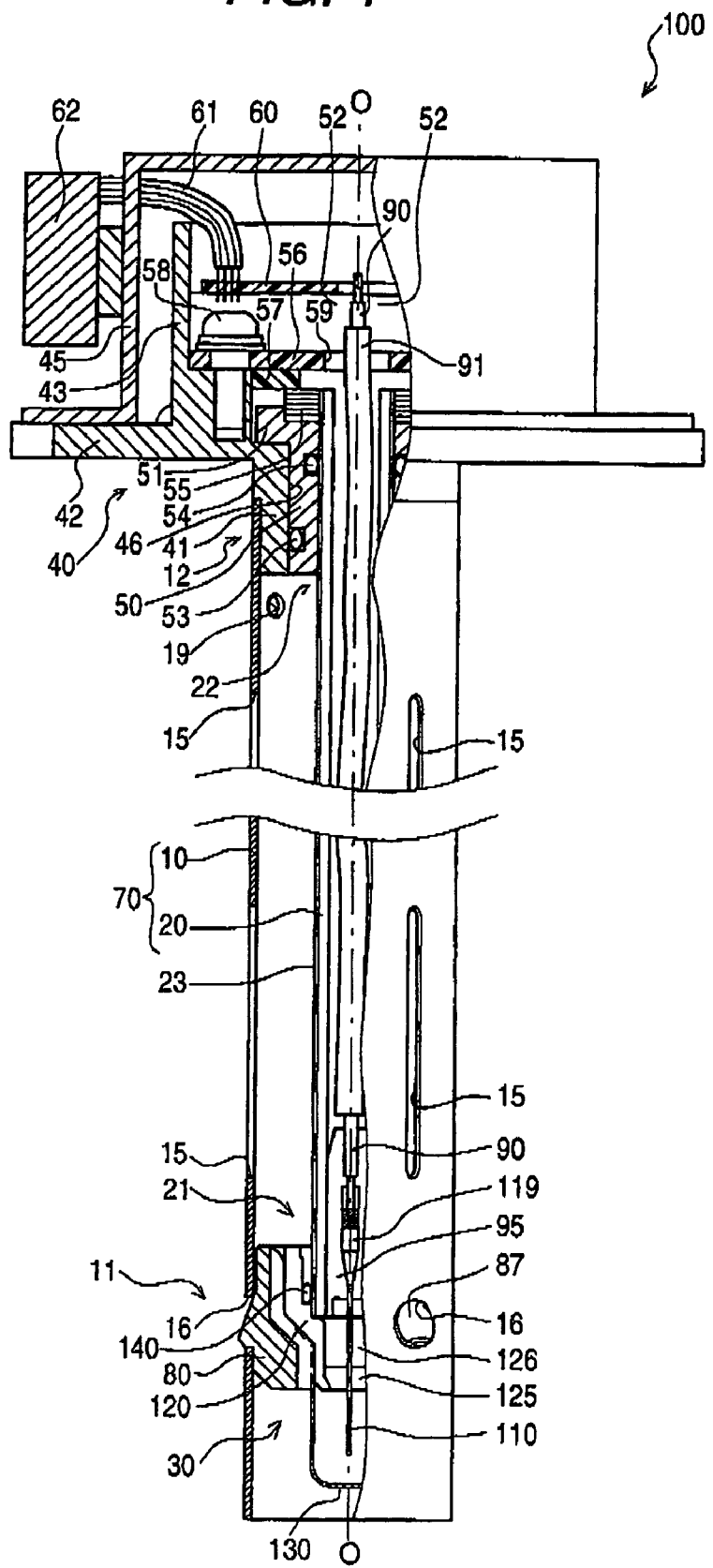
FIG. 1 is a partial cutaway sectional view of a liquid state detecting sensor 100.

Reference numerals used to identify various structural features in the drawings include the following.
10: outer cylindrical electrode
20: inner electrode
70: level detecting part
98: urea-water tank
100: liquid state detecting sensor
110: ceramic heater
114: heating resistor
221: CPU
301: level fluctuation storage area

DETAILED DESCRIPTION OF THE INVENTION

A mode for carrying out the invention or an embodiment of a liquid state detecting apparatus according to the invention will now be described. However, the present invention should not be construed as being limited hereto.

Figure 2:
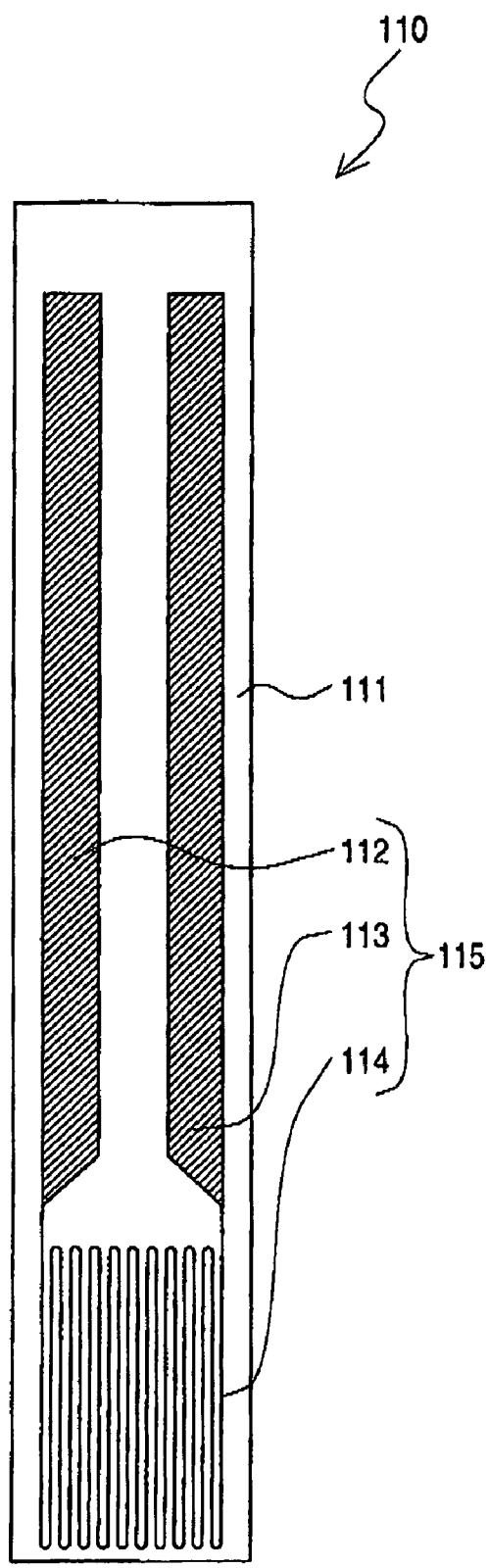
FIG. 2 is a schematic view of a heater pattern 115 of a ceramic heater 110.

First, a structure of a liquid state detecting sensor 100 will be described by way of example with reference to FIGS. 1 and 2. FIG. 1 is a partial cutaway vertical sectional view of the liquid state detecting sensor 100. FIG. 2 is a schematic view of a heater pattern 115 of a ceramic heater 110. The longitudinal direction of a level detecting part 70 (a capacitor formed by an outer cylindrical electrode 10 and an inner electrode 20) of the liquid state detecting sensor 100 is taken as the direction of an O-axis. Also, the side of the sensor where a liquid property detecting part 30 is provided constitutes a tip side and the side of the sensor where a mounting part 40 is provided constitutes a back end side. The outer cylindrical electrode 10 and the inner electrode 20 correspond to the "first electrode" and "second electrode," respectively.

The liquid state detecting sensor 100 of the present embodiment is a sensor for detecting the state of an aqueous urea solution used for reducing a nitrogen oxide (NOx) contained in an exhaust gas from a diesel automobile, specifically, the level of the aqueous urea solution (liquid level), the temperature of the solution, and the concentration of urea as a particular component included in the solution. As shown in FIG. 1, the liquid state detecting sensor 100 includes a level detecting part 70 formed by an outer cylindrical electrode 10 and a cylindrical inner electrode 20 provided inside the outer cylindrical electrode 10 in the O-axis direction of the outer cylindrical electrode 10, the liquid property detecting part 30 provided on the tip side of the internal electrode 20, and the mounting part 40 for mounting the liquid state detecting sensor 100 in a urea-water tank 98 (see FIG. 3).

The outer cylindrical electrode 10 is made of metal in the form of an elongate cylinder extending in the O-axis direction. A plurality of narrow slits 15 are intermittently provided on the outer circumference of the outer cylindrical electrode 10 along each of three generating lines at equal intervals in the circumferential direction. An opening 16 is provided on each of the generating lines along which the slits 15 are formed, the openings 16 being provided at a tip part 11 of the outer cylindrical electrode 10 to prevent a rubber bush 80, to be described later, interposed between the outer electrode and the inner electrode 20 from coming off. Further, one air vent hole 19 is formed in a position of the outer cylindrical electrode 10 near a base end 12 on the back end side thereof, the vent hole being formed on a generating line different from the generating lines along with the slits 15 are formed. The tip part 11 of the outer cylindrical electrode 11 extends beyond the position of the openings 16 in the O-axis direction so as to surround the periphery of a ceramic heater 110 of the liquid property detecting part 30, which will be described later, in the radial direction thereof, the tip part surrounding the ceramic heater 110 together with a protector 130 covering and protecting the heater. The extreme end of the electrode (the lowermost part in the figure) is open, and the protector 130 forming a part of the liquid property detecting part 30 can be seen through the opening.

The outer cylindrical electrode 10 is welded with the base end thereof engaged with the periphery of an electrode support portion 41 of the mounting part 40 made of metal. The mounting part 40 serves as a base for securing the liquid property detecting part 100 on a urea-water tank 98 as a liquid container, and a mounting hole (not shown) to insert a mounting bolt is formed on a flange portion 42 of the same. A housing portion 43 is formed on the side of the mounting part 40 opposite the electrode support portion 41 with the flange portion 42 interposed between them, the housing portion housing a circuit board 60, to be described later, carrying a circuit for detecting the level, temperature, and urea concentration of an aqueous urea solution and an input/output circuit for electrical connection with an external circuit which is not shown (e.g., an engine controller (ECU) of an automobile). The outer cylindrical electrode 10 is grounded through the mounting part 40.

The circuit board 60 is placed on board placing parts (not shown) protruding from four corners of an inner wall of the housing portion 43, The housing portion 43 is covered and protected by a cover 45, and the cover 45 is secured to the flange portion 42. A connector 62 is secured on a side surface of the cover 45, and connection terminals (not shown) of the connector 62 are connected with patterns (an input/output circuit part 290 to be described later) on the circuit board 60 through wiring cables 61. The circuit board 60 and an ECU are connected through the connector 62.

A hole 46 penetrates through the electrode support portion 41 of the mounting part 40 into the housing portion 43, and the base end 22 of the inner electrode 20 is inserted into the hole 46. The inner electrode 20 of the present embodiment is made of a metal material in the form of an elongate cylinder extending in the O-axis direction. An insulation film 23 made of a fluorine type resin such as PTFE, PFA or ETFE, an epoxy resin or a polyimide resin is formed on an outer circumferential surface of the inner electrode 20. The insulation film 23 is provided in the form of a resin coating layer by performing dipping or electrostatic powder coating to apply such a resin on the outer surface of the inner electrode 20 and heating the resin. A capacitor whose electrostatic capacity changes according to the level of the aqueous urea solution is formed between the inner electrode 20 and the outer cylindrical electrode 10, whereby a level detecting part 70 is provided.

The base end 22 on the back end side of the inner electrode 20 in the O-axis direction is engaged with a pipe guide 55 and an inner case 50 for securing the inner electrode 20 to the mounting part 40. The pipe guide 55 is an annular guide member bonded to the inner electrode 20 near an edge of the base end 22. The inner case 50 is a member made of resin in the form of a flanged cylinder for positioning and supporting the inner electrode 20 such that the inner electrode 20 and the outer cylindrical electrode 10 are reliably insulated from each other, and a tip part of the same engages the hole 46 of the electrode support portion 41 of the mounting part 40. The inner case 50 is formed with a flange portion S1 protruding outwardly in the radial direction of the case, and the inner case 50 is engaged with the electrode support portion 41 by inserting it into the hole 46 of the electrode support portion 41 from the side of the housing portion 43. The flange portion 51 abuts on an inner bottom surface of the housing portion 43 to prevent the inner case 50 from passing through the hole 46. The inner electrode 20 is inserted into the inner case 50 from the side of the housing portion 43, and is prevented by coming out of the inner case 50 by means of the pipe guide 55 which abuts the flange portion 51.

Further, an O-ring 53 and an O-ring 54 are provided on the outer and inner circumferences of the inner case 50, respectively. The O-ring 53 seals the gap between the inner circumference of the inner case 50 and the outer circumference of the base end 22 of the inner electrode 20. As a result, when the liquid state detecting sensor 100 is mounted in the urea-water tank 98 (see FIG. 3), the urea-water tank 98 is kept watertight and airtight such that there is communication between the inside and outside of the same through the housing portion 43. A sheet-like seal member, which is not shown, is attached to a surface near the end of the flange portion 42 of the mounting part 40 to maintain water-tightness and air-tightness between the flange portion 42 and the urea-water tank 98 when the liquid state detecting sensor 100 is mounted in the urea-water tank.

When the inner electrode 20 is assembled to the mounting part 40, the pipe guide 55 is urged against the flange portion 51 of the inner case 50 by two presser plates 56 and 57. The presser plate 56 having insulating properties is secured in the housing portion 43 with the presser plate 57 sandwiched between the plate 56 and the pipe guide 55 to urge the pipe guide 55. As a result, the inner electrode 20 bonded to the pipe guide 55 is secured to the electrode supporting portion 41. The presser plates 56 and 57 have a hole 59 as shown in the present embodiment. An electrode lead-out wire 52 of the inner electrode 20 and a two-core cable 91 including two lead wires 90 (only one of the lead wires 90 is shown in FIG. 1) for electrical connection with the ceramic heater 110 to be described later are inserted through the hole and electrically connected to respective patterns on the circuit board 60. An electrode (not shown) on a ground side of the circuit board 60 is connected to the mounting part 40, and the outer cylindrical electrode 10 welded to the mounting part 40 is therefore electrically connected to the ground side.

In the present embodiment, the liquid property detecting part 30 provided at the tip part 21 of the inner electrode 20 comprises a ceramic heater 110 as a detecting element for detecting the temperature of the aqueous urea solution and the concentration of urea included in the same, a holder 120 made of an insulating resin mounted on the tip part 21 of the inner electrode 20, and a protector 130 which covers the periphery of the ceramic heater 110 exposed from the holder 120 to protect the same.

As shown in FIG. 2, the ceramic heater 110 is provided by forming a heater pattern 115 primarily made of Pt on a sheet-like ceramic substrate 111 made of ceramic having insulating properties and embedding the heater pattern 115 by sandwiching it between the substrate 111 and another ceramic substrate (not shown) paired with the same. The pattern constituting the heating resistor 114 is provided with a sectional area smaller than that of patterns constituting lead portions 112 and 113 serving as two poles for applying a voltage, whereby heat is generated primarily at the heating resistor 114 when energized. Through holes (not shown) each penetrating the surface of the ceramic substrate 111 are provided on both ends of the lead portions 112 and 113 and electrically connected to two connectors 119 which relay the connection to the two lead wires 90, respectively (FIG. 1 shows only one each of those elements).

As shown in FIG. 1, the holder 120 supporting the ceramic heater 110 is in the form of a cylinder having a stepped configuration provided by two outer diameters. The ceramic heater 110 is secured at the tip side of the holder having the smaller diameter with securing members 125 and 126 constituted by an adhesive so as to expose the side of the ceramic heater where the heating resistor 114 is embedded. The back end side of the holder having the greater diameter is attached to the tip part 21 of the inner electrode 20, and a seal ring 140 is interposed between the outer circumferential surface of the inner electrode 20 and the inner circumferential surface of the holder 120 to maintain the water-tightness and air-tightness of the interior of the inner electrode 20.

Before the holder 120 is mounted, the core wires of the two lead wires 90 of the cable 91 are crimped or soldered to the respective connectors 119 of the ceramic heater 110. Further, the connectors 119 and the lead wires 90 are covered and protected by a protective member 95 having insulating properties including the bonded regions thereof The two lead wires 90 are inserted into the cylindrical inner electrode 20 and connected to the circuit board 60.

The protector 130 is a protective member made of metal and formed in the shape of a bottomed cylinder. An open side of the protector is fitted to the outer circumference of the part of the holder 120 having the small diameter. A liquid communication hole (not shown) is provided on the outer circumference of the protector 130 to allow the aqueous urea solution to be exchanged between the inside and outside of the protector 130.

The liquid property detecting part 30 having such a configuration is mounted on the tip part 21 of the inner electrode 20 with the holder 120 interposed, and it is elastically supported in the outer cylindrical electrode 10 by a rubber bushing 80. The rubber bushing 80 has a cylindrical shape, and it is secured by engaging a protrusion 87 formed on an outer circumferential surface thereof with the opening 16 of the outer cylindrical electrode 10. A plurality of grooves (not shown) is provided in the O-axis direction on each of the outer and inner circumferential surfaces of the rubber bushing 80 When the liquid state detecting sensor 100 is mounted in the urea-water tank 98, the grooves allow liquid exchange between parts of the aqueous urea solution which have flowed into the tip side and back end side of the rubber bushing and also allow air bubbles to be removed from the solution. The rubber bushing 80 allows the liquid property detecting part 30 and the level detecting part 70 to be integrally formed and insulated from one another.

Figure 3:
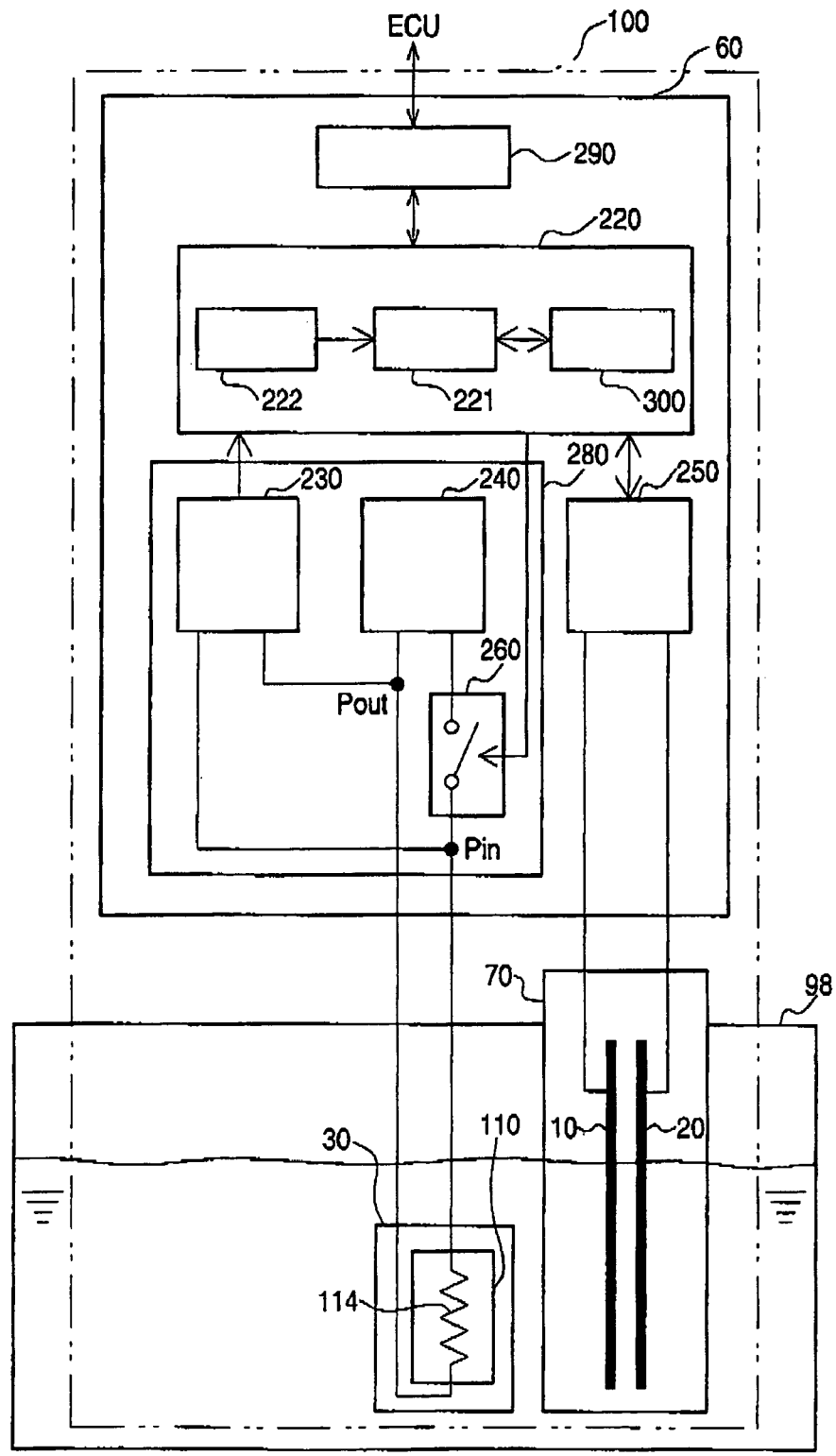
FIG. 3 is a block diagram showing an electrical configuration of the liquid sensor detecting sensor 100.
Figure 4:
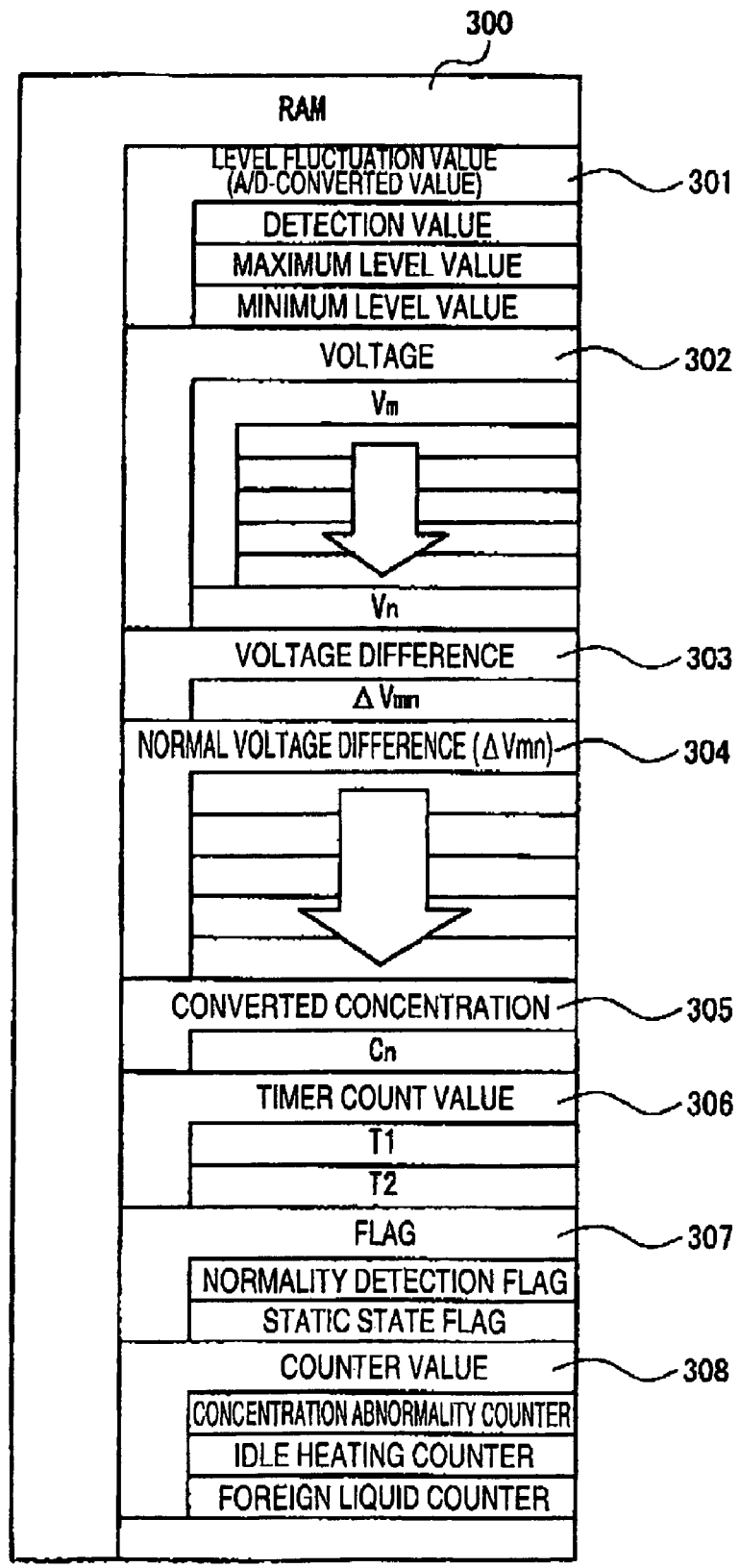
FIG. 4 shows a conceptual configuration of storage areas of a RAM 300.

An electrical configuration of the liquid state detecting sensor 100 will now be described with reference to FIGS. 3 and 4. FIG. 3 is a block diagram showing the electrical configuration of the liquid state detecting sensor 100. FIG. 4 shows a conceptual configuration of a storage area of a RAM 300.

As shown in FIG. 3, the liquid state detecting sensor 100 is mounted to the urea-water tank 98 as a liquid container. The level detecting part 70 having a pair of electrodes (the outer cylindrical electrode 10 and the inner electrode 20) and the liquid property detecting part 30 having the ceramic heater 110 having the heating resistor 114 embedded therein are immersed in the aqueous urea solution contained in the urea-water tank 98 as a liquid whose state is to be detected. A microcomputer 220 is mounted on the circuit board 60 of the liquid state detecting sensor 100, and a level detection circuit unit 250 for controlling the level detecting part 70, a liquid property detection circuit unit 280 for controlling the liquid property detecting part 30, and an input/output circuit unit 290 for communication with an ECU are connected to the microcomputer.

The microcomputer 220 includes a CPU 221, a ROM 222, and a RAM 300 having known configurations. The CPU 221 controls the liquid state detecting sensor 100. The ROM 222 includes various storage areas which are not shown, and a state detection program and Expressions (1) to (5) to be described later, initial values of various parameters, and thresholds are stored in predetermined storage areas. Similarly, the RAM 300 includes various storage areas to be described later as shown in FIG. 4, part of the state detection program, various parameters, and timer count values are temporarily stored when the state detection program is executed.

The input/output circuit unit 290 controls a communication protocol for inputting and outputting signals between the liquid state detecting sensor 100 and the ECU. The level detection circuit unit 250 is a circuit which applies an AC voltage between the outer cylindrical electrode 10 and the inner electrode 20 of the level detecting part 70 based on an instruction from the microcomputer 220 to convert a current which has flowed through the capacitor constituting the level detecting part 70 into a voltage. The circuit unit further performs A-D conversion of the voltage and outputs it to a microcomputer 220.

The liquid property detection circuit unit 280 comprises a circuit unit which passes a constant current through the ceramic heater 110 of the liquid property detection part 30 based on an instruction from the microcomputer 220, and outputs a resultant detection voltage generated across the heating resistor 114 to the microcomputer 220. The liquid property detecting circuit unit 280 comprises a differential amplifier circuit 230, a constant current outputting part 240, and a switch 260.

The constant current outputting part 240 outputs the constant current passed through the heating resistor 114. The switch 260 is provided on the path for energization of the heating resistor 114 and opened and closed under control of the microcomputer 220. The differential amplifier circuit 230 outputs a difference between a potential Pin appearing at one end of the heating resistor 114 and a potential Pout appearing at another end of the resistor to the microcomputer 220 as a detection voltage.

The storage areas of the RAM 300 will now be described. As shown in FIG. 4, the RAM 300 includes level fluctuation storage areas 301, voltage storage areas 302, a voltage difference storage area 303, normal voltage difference storage areas 304, a converted concentration storage area 305, timer count value storage areas 306, flag storage areas 307, and counter value storage areas 308.

Stored in the level fluctuation storage areas 301 are detection values (A-D converted values) representing the level of the aqueous urea solution obtained by A-D converting the output of the level detecting part 70 at the level detection circuit unit 250 and a maximum value, and a minimum value of level detection values obtained by repeating level detection according to the state detection program which will be described later. The output of the liquid property detection part 30 (i.e., the difference between the potential Pin and the potential Pout) is input to the microcomputer 220 through the differential amplifier circuit 230 as a detection voltage, and a voltage Vm detected 10 msec after the start of urea concentration measurement and a voltage Vn detected 700 msec after the start of measurement are stored in the voltage storage area 302. Five storage areas are provided as areas for storing the voltage Vm. The most recent five voltages among voltages repeatedly detected according to the state detection program to be described later are stored, and the voltages detected prior thereto are discarded.

A difference ΔVmn between the most recent voltages Vm and Vn stored in the voltage storage areas 302 is stored in the voltage difference storage area 303. A voltage difference ΔVmn which has resulted in a determination by the state detection program that there is no abnormality in a detected concentration of the aqueous urea solution is stored in a normal voltage difference storage area 304. Five normal voltage difference storage areas 304 are similarly provided to store the most recent five voltage differences ΔVmn. A concentration-converted value Cn calculated from a voltage difference Δmn is stored in the converted concentration storage area 305.

Timer count value storage areas 306 store initial values of two types of timers T1 and T2 used by the state detection program, and count values from a timer program (not shown) which is separately executed are stored in the areas when the timers are reset. When a lapse of a predetermined time (e.g., 1 sec) is confirmed by the state detection program to be described later, the confirmation is made by determining whether differences between the initial values of the timers T1 and T2 stored at the time of a reset and the count value of the timer program at the time of confirmation is greater than a value corresponding to the predetermined time.

The values of a normality detection flag and a static state flag used by the state detection program are stored in the flag storage areas 307. A count value of each of a concentration abnormality counter, an idle heating counter, and foreign liquid counter is stored in a counter value storage area.

The RAM 300 is also provided with various storage areas which are not shown, and the state detection program that uses each of the above-described parameters is read in a predetermined storage area and executed.

Figure 5:
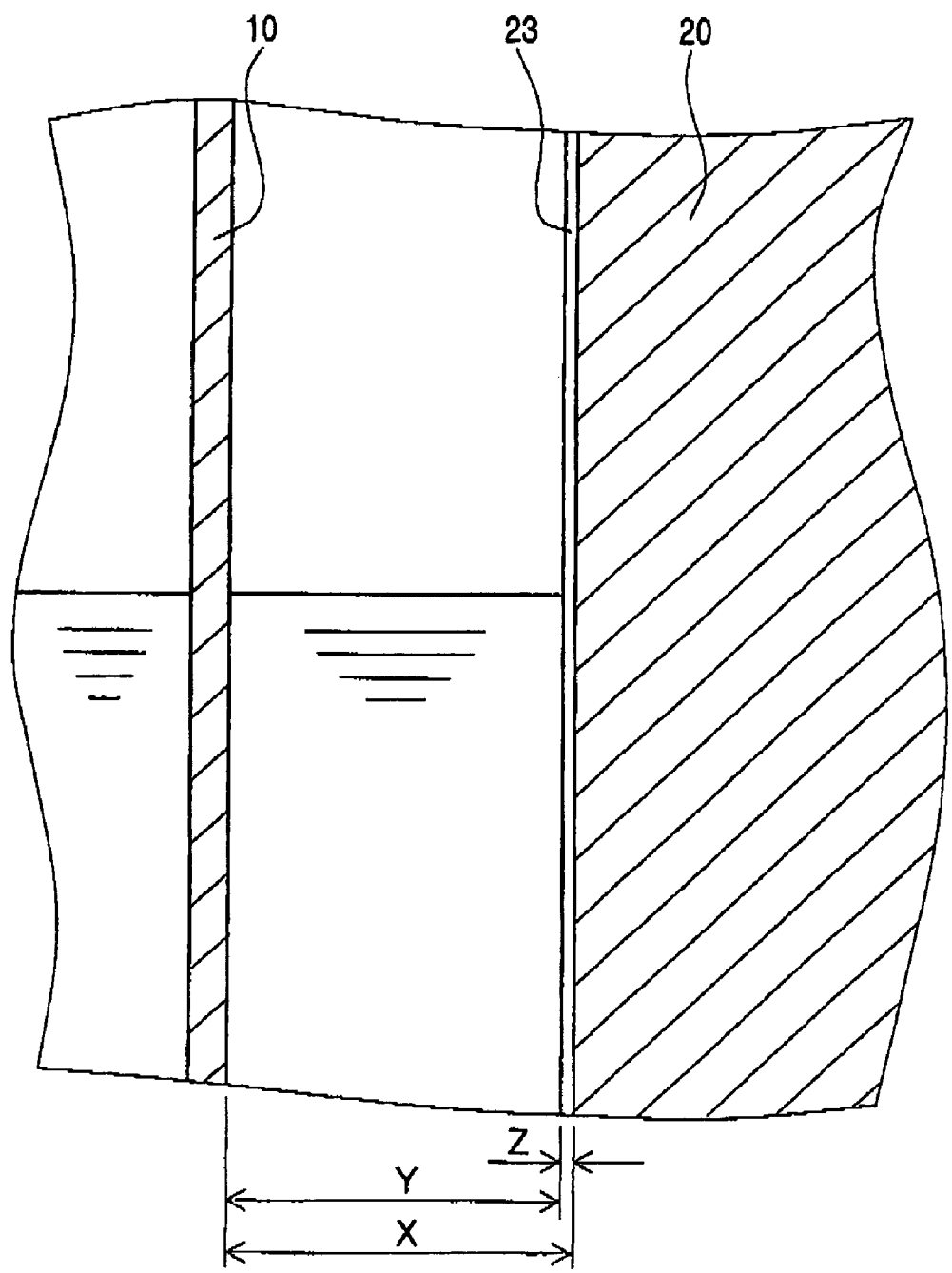
FIG. 5 is an enlarged sectional view in the vicinity of the surface of an aqueous urea solution that fills a gap between an outer cylindrical electrode 10 and an inner electrode 20.

The principles of detection of the level, temperature, and urea concentration of an aqueous urea solution by the liquid state detecting sensor 100 of the present embodiment will now be described. First, the principle of detection of the level of an aqueous urea solution performed by the level detecting part 70 will be described with reference to FIG. 5. FIG. 5 is an enlarged sectional view in the vicinity of the surface of an aqueous urea solution that fills the gap between the outer cylindrical electrode 10 and the inner electrode 20.

The liquid state detecting sensor 100 (see FIG. 1) is assembled to the urea-water tank (see FIG. 3) containing the aqueous urea solution with the tips of the outer cylindrical electrode 10 and the inner electrode 20 pointing toward the bottom wall of the tank. Specifically, the level detecting part 70 of the liquid state detecting sensor 100 is assembled to the urea-water tank 98 such that the tip side of the outer cylindrical electrode 10 and the inner electrode 20 is on the side of the tank in which the volume of the aqueous urea solution is smaller (a low-level side) where the direction of displacement of the aqueous urea solution whose volume changes in the urea-water tank 98 (the direction in which the level of the aqueous urea solution increases and decreases) is the O-axis direction. The electrostatic capacity at the gap between the outer cylindrical electrode 10 and the inner electrode 20 is measured to detect the level of the aqueous urea solution present in the gap in the O-axis direction. The principle is based on the known fact that a static capacity between two points having different potentials in the radial direction becomes greater, the smaller the difference between the diameters at those points.

As shown in FIG. 5, in a region which is not filled with the aqueous urea solution, the distance between positions resulting in a potential difference in the gap is the sum of a distance (referred to as a distance Y) corresponding to the thickness of the layer of air intervening between the inner circumferential surface of the inner electrode 10 and the insulation film 23 and a distance (referred to as a distance Z) corresponding to the thickness of the insulation film 23 (the sum is referred to as a distance X). In a region filled with the aqueous urea solution, the distance between positions resulting in a potential difference in the gap is the distance Z corresponding to the thickness of the insulation film 23 because the aqueous urea solution is electrically conductive which makes the potentials at the outer cylindrical electrode 10 and the aqueous urea solution substantially equal to each other.

In other words, the electrostatic capacity of the gap in the region which is not filled with the aqueous urea solution is the composite electrostatic capacity of a capacitor provided by series-connecting a capacitor whose electrode distance is the distance Y and whose dielectric element (non-conductor) is air and a capacitor whose electrode distance is the distance Z and whose dielectric element is the insulation film 23. The electrostatic capacity of the gap in the region filled with the aqueous urea solution is the electrostatic capacity of a capacitor whose electrode distance is the distance Z and whose dielectric element is the insulation film 23. The electrostatic capacity of a capacitor formed by connecting those capacitors in parallel is measured as the electrostatic capacity of the level detecting part 70 as a whole.

Since the distance Y is greater than the distance Z, the electrostatic capacity per unit between electrodes in which air serves as a dielectric element is smaller than the electrostatic capacity per unit between electrodes in which the insulation film 23 serves as a dielectric element. Therefore, a change in the electrostatic capacity of the region filled with the aqueous urea solution is greater than a change in the electrostatic capacity of the region which is not filled with the aqueous urea solution, and the capacitor as a whole formed by the outer cylindrical electrode 10 and the inner electrode 20 has an electrostatic capacity that is proportional to the level of the aqueous urea solution.

The measurement of the level of the aqueous urea solution as thus described is carried out by the microcomputer 220 connected to the level detecting part 70 through the level detection circuit unit 250, and a resultant level information signal is output from the input/output circuit unit 290 to an ECU which is not shown.

Figure 6:
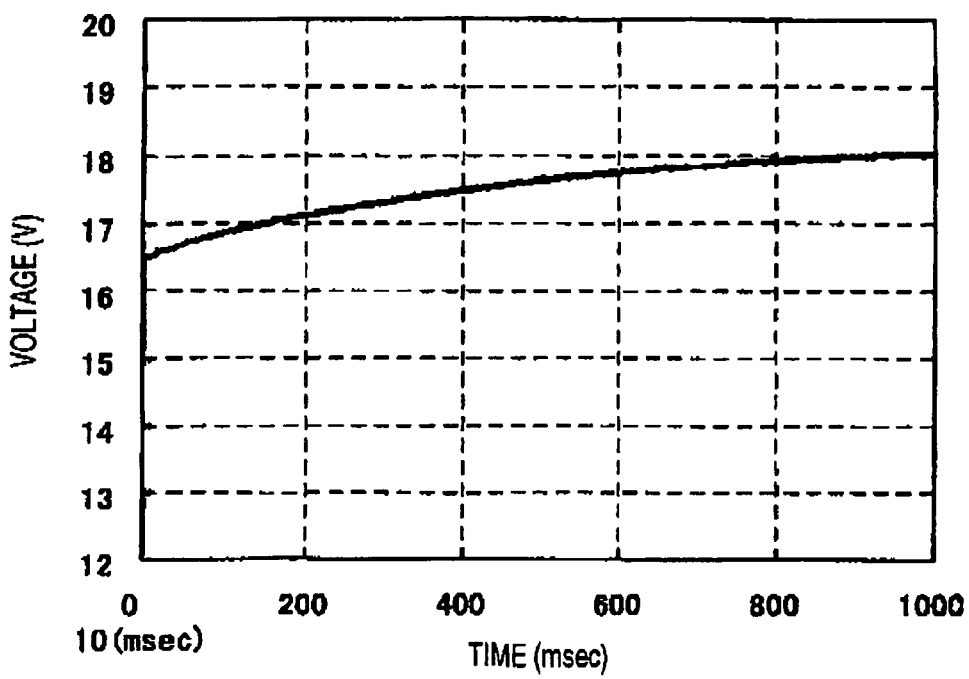
FIG. 6 is a graph of an exemplary aqueous urea solution having a urea concentration of 32.5% by weight at a temperature of 25° C., the graph showing how a voltage associated with the resistance of a heating resistor increases with an increase in the temperature of the heating resistor following start of energization of the heating resistor upon application of a constant current.
Figure 7:
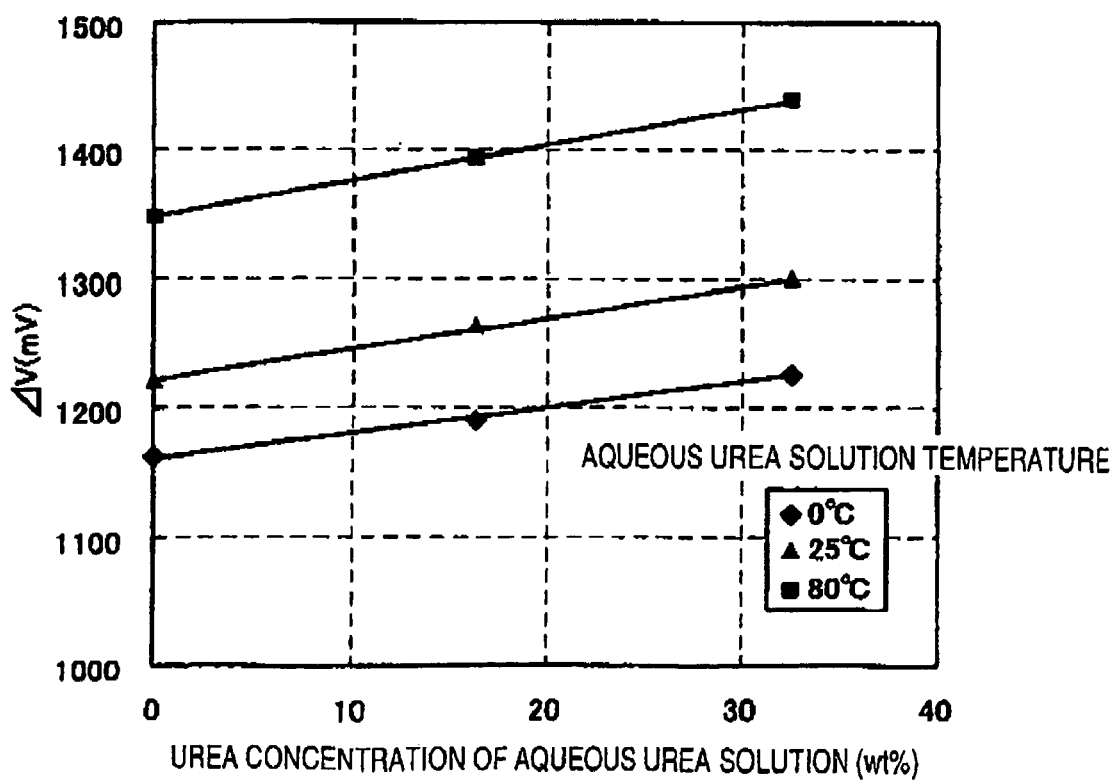
FIG. 7 is a graph showing that a voltage change ΔV at the heating resistor is proportional to the urea concentration of the aqueous urea solution and is temperature-dependent.
Figure 8:
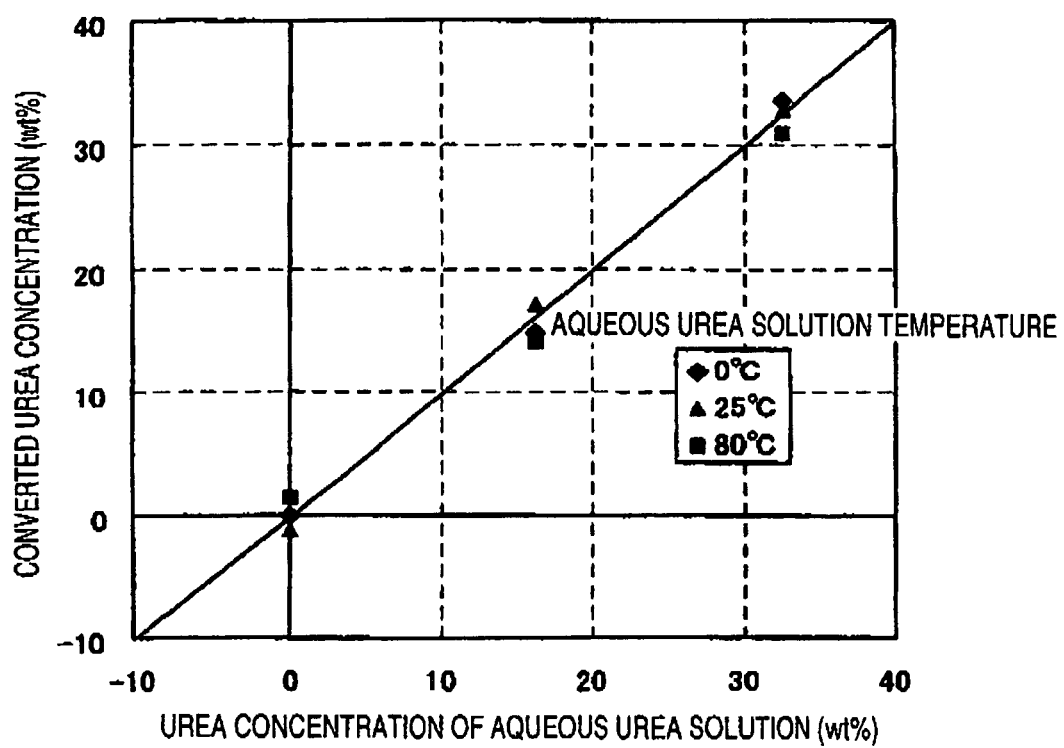
FIG. 8 is a graph showing that a corrected concentration (converted concentration) and the actual urea concentration substantially agree with each other when the relationship between the voltage change ΔV at the heating resistor and the urea concentration of the aqueous urea solution is corrected with reference to the temperature of the aqueous urea solution.

A description will now be made with reference to FIGS. 6 to 8 on the principle of detection of the temperature of the aqueous urea solution and the concentration of urea as a particular component included in the aqueous urea solution at the ceramic heater 110 forming a part of the liquid property detecting part 30. FIG. 6 is a graph of an exemplary aqueous urea solution having a urea concentration of 32.5% by weight at a temperature of 25° C., the graph showing how a voltage associated with the resistance of the heating resistor increases with an increase in temperature of the heating resistor as time passes following start of energization of the heating resistor upon application of a constant current. FIG. 7 is a graph showing that a voltage change $\Delta V$ at the heating resistor is proportional to the urea concentration of the aqueous urea solution and is temperature-dependent. FIG. 8 is a graph showing that a corrected concentration (converted concentration) and the actual urea concentration substantially agree with one another when the relationship between the voltage change $\Delta V$ at the heating resistor and the urea concentration of the aqueous urea solution is corrected with reference to the temperature of the aqueous urea solution.

The temperature of the heating resistor itself is substantially the same as the temperature of the liquid surrounding the heating resistor immediately after the start of energization. This is because little heat is generated in that period. As indicated by the graph of FIG. 6, after a constant current starts flowing through the heating resistor (it should be noted that it takes about 10 msec for the current to stabilize after the energization is started), the temperature of the heating resistor itself continuously increases as time passes.

Thus, the temperature of the aqueous urea solution can be measured when there is prior knowledge of a correlation between the voltage at the heating resistor corresponding to the resistance thereof after the start of energization and the temperature of the aqueous urea solution surrounding the resistor. The relationship between the resistance of the heating resistor after energization of the same and the temperature of the aqueous urea solution surrounding the resistor is represented by the following expression.

$$R_T = R_0(1 + \alpha_0 T) \qquad \text{Expression 1}$$

RT represents the resistance of the beating resistor at a temperature T° C., and the liquid surrounding the heating resistor is also T° C. when energization of the heating resistor commences. $R_0$ represents the resistance ($\Omega$) of the heating resistor at 0° C. $\alpha_0$ represents a temperature coefficient with reference to 0° C., and the coefficient is determined by the material of the heat resistor. Therefore, it is apparent from Expression 1 that the resistance of the heating resistor is proportional to the ambient temperature.

The resistance is also expressed as follows according to Ohm's law.

$$R_T = V_T/I \qquad \text{Expression 2}$$

The current I($\Lambda$) is constant because a constant current is passed through the heating resistor. That is, Expression 2 indicates that the voltage $V_T$ of the heating resistor (a voltage (V) output by the differential amplifier circuit unit 230 in the present embodiment) is proportional to the resistance RT($\Omega$), and Expression 1 indicates that the voltage is proportional to the ambient temperature.

When energization of the heating resistor is continued, the temperature of the heating resistor rises above the temperature of the surrounding liquid, and the quantity of heat conducted from the heating resistor to the surrounding liquid depends on the thermal conductivity of the liquid. That is, the temperature-rise rate of the heating resistor depends on the thermal conductivity of the liquid surrounding the same. It is known that the thermal conductivity of a liquid depends on the concentration of a particular component included in the liquid. Therefore, when the heating resistor is immersed in a liquid and the liquid is heated for a certain period of time, a change in the thermal conductivity of the liquid surrounding the resistor can be found by determining the degree of change in the resistance of the heating resistor, whereby the concentration of the liquid can be determined.

The above description is represented by the graph of FIG. 7. For example, assume that a heating resistor is immersed on an aqueous urea solution at a temperature of 25° C. is energized for 700 msec. Then, when the urea concentration of the aqueous urea solution is 0% by weight, the heating resistor undergoes a voltage change of 1220 mV (e.g., a change in voltage drop across the resistor when a constant current is passed through the resistor) associated with a change in the resistance thereof. Urea concentrations of 16.25% and 32.5% by weight result in voltage changes of 1262 mV and 1298 mV, respectively. That is, an increase in the urea concentration of the aqueous urea solution results in lower thermal conductivity, which suppresses the conduction of heat away from the heating resistor and increases the temperature rise rate of the same. As a result, the heating resistor undergoes a greater resistance change and a greater voltage change (indicated by $\Delta V$ in the figure) associated with the resistance change.

It will be understood from above that there is a proportional relationship as shown in FIG. 7 between the urea concentration of the aqueous urea solution and a change in the resistance (e.g., as measured by a change in voltage drop across the resistor) of the heating resistor. The following expression represents the relationship between the urea concentration of the aqueous urea solution around the heating resistor and the voltage change $\Delta$ associated with the resistance change of the heating resistor.

$$\Delta V = a_T C + b_T \qquad \text{Expression 3}$$

where $\Delta V$ represents a difference (mV) between a voltage associated with the resistance of the heating resistor detected after the energization is started and a voltage associated with the resistance detected after a certain detection time (e.g., 700 msec) has elapsed after energization has started; C represents the concentration of urea (% by weight) in the aqueous urea solution; and $a_T$ represents an intercept of the slope of a line $\Delta V$-C taken when the aqueous urea solution is at a temperature T° C.

Even when the concentration of urea contained in the aqueous urea solution remains unchanged, a change in the temperature of the aqueous urea solution results in a change in the temperature rise rate (or the voltage change ΔV) of the heating resistor. That is, the temperature rise rate of the heating resistor also depends on the temperature of the aqueous urea solution.

The above description is also represented by a graph in FIG. 7. For example, when the heating resistor is energized for 700 msec to heat an aqueous urea solution at a temperature of 25° C. having a urea concentration of 32.5% by weight, there is a voltage change ΔV of 1298 mV associated with a resistance change of the heating resistor. On the contrary, when an aqueous urea solution at a temperature of 80° C. having the same concentration is energized for 700 msec, there is a voltage change ΔV of 1440 mV. That is, when the urea concentration of an aqueous urea solution remains unchanged, the heating resistor undergoes a smaller resistance change and hence a smaller voltage change ΔV associated with the resistance change, the lower the starting temperature of the aqueous urea solution.

As shown above, the relationship between the urea concentration of an aqueous urea solution and a resistance change (voltage change ΔV) of a heating resistor depends on the temperature of the aqueous urea solution. Therefore, the urea concentration can be accurately calculated by correcting (calibrating) Expression 1 with reference to the temperature of the aqueous urea solution obtained from Expressions 1 and 2. Expressions for making such a correction with reference to the temperature of the aqueous urea solution are shown below.

$$a_T = a_{25} + x(T-25) \quad \text{Expression 4}$$

$$b_T = b_{25} + x(T-25) \quad \text{Expression 5}$$

where $a_{25}$ represents the slope of a line ΔV-C taken when the temperature of the aqueous urea solution is 25° C.; and x represents a temperature correction coefficient for the slope of the line. Similarly, $b_{25}$ represents an intercept of the slope of the line ΔV-C taken when the temperature of the aqueous urea solution is 25° C.; and y represents a temperature correction coefficient for the intercept of the line.

Experiments identified correction values $a_{25}=2.3$, $b_{25}=1.223$, $x=0.015$, and $y=2.45$ giving good results for Expressions 3, 4, and 5. FIG. 8 indicates that a concentration of an aqueous urea solution obtained by a correction using those values (a converted concentration) substantially agrees with the actual concentration of urea.

Figure 13:
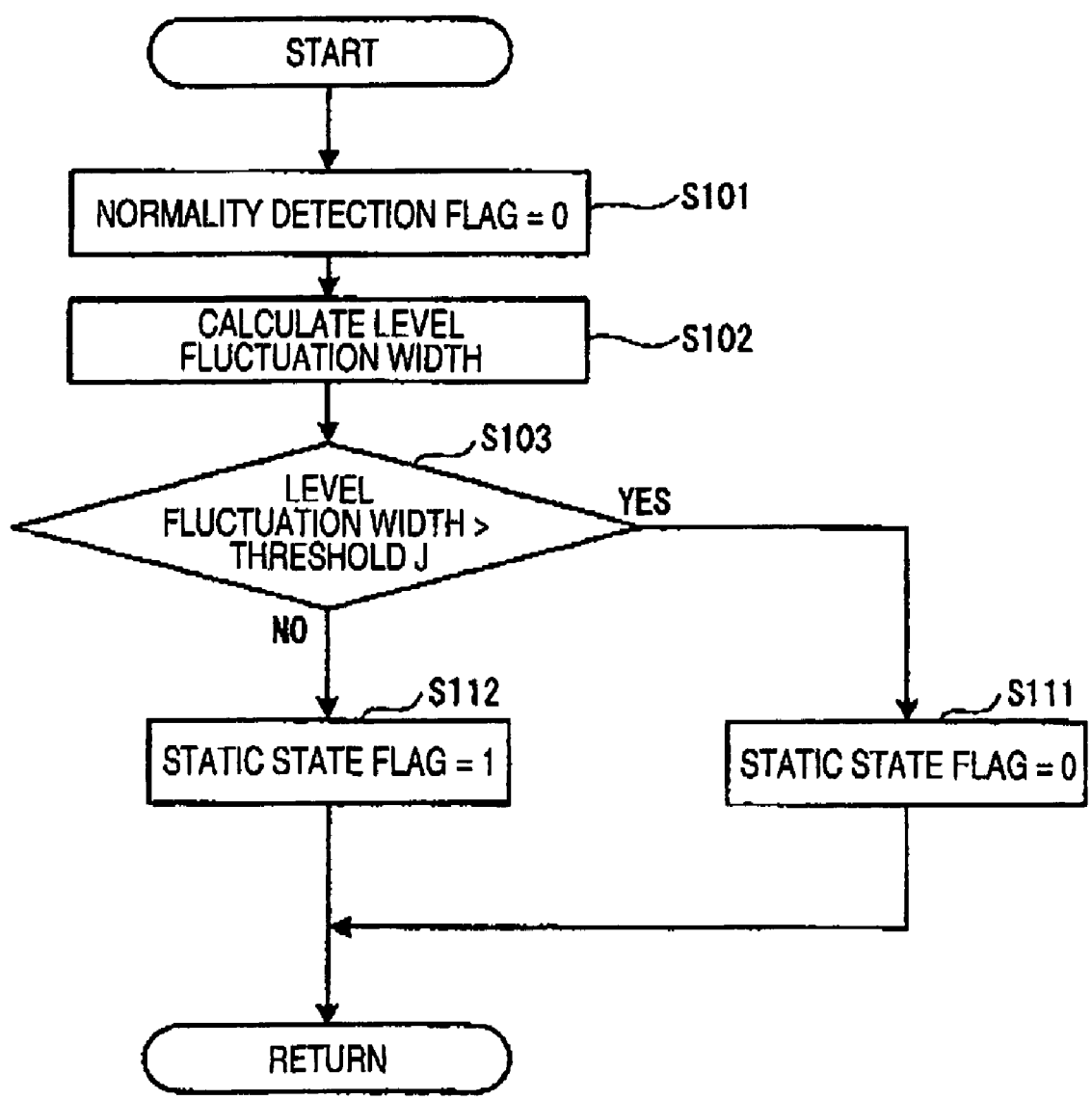
FIG. 13 is a flow chart of a static state determination subroutine.
Figure 14:
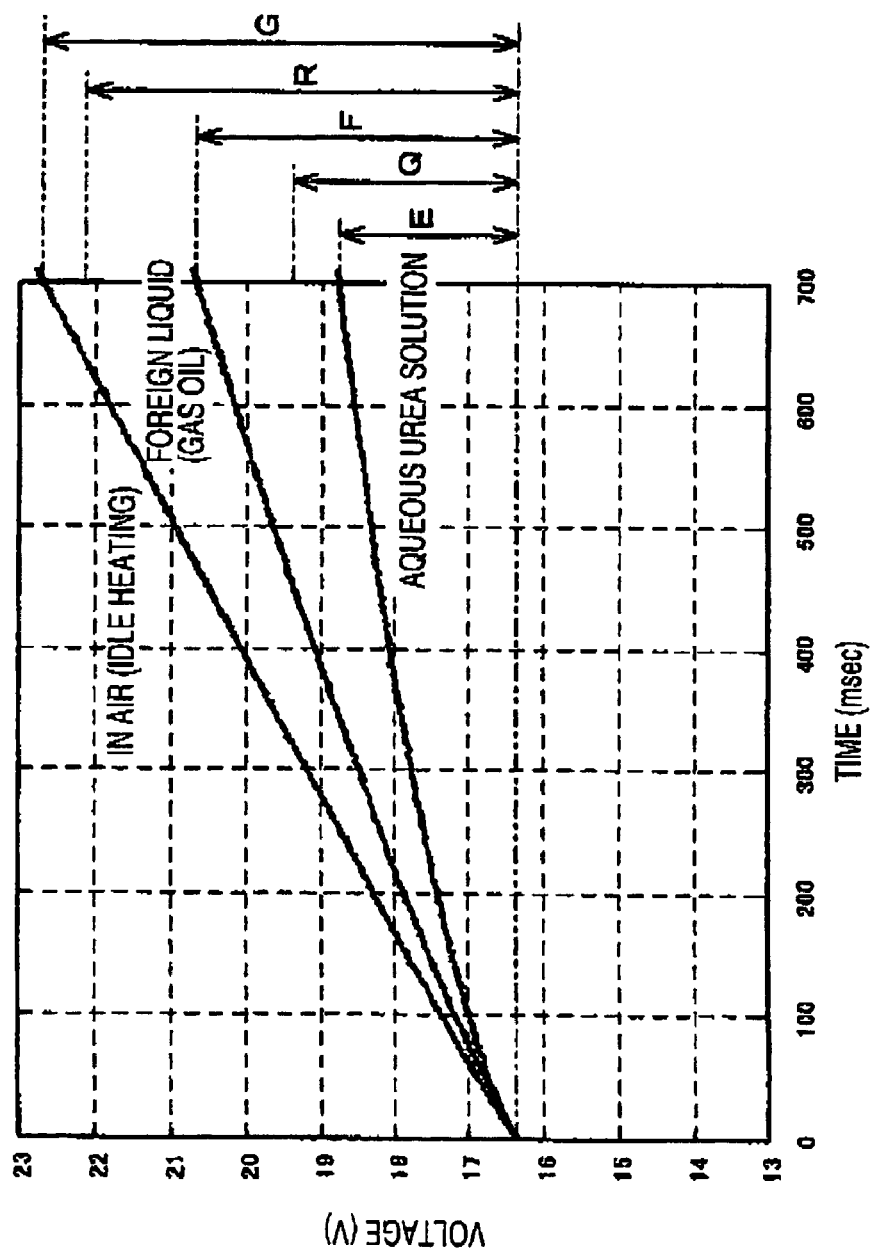
FIG. 14 is a graph for explaining thresholds Q and R for detecting idle heating and the presence of a foreign liquid.

The liquid state detecting sensor 100 of the present embodiment detects the level, temperature, and urea concentration of an aqueous urea solution based on such principles. The state detection program will now be described with reference to FIG. 3, FIG. 4, and FIGS. 9 to 14. FIGS. 9 to 12 are a flow chart of a main routine of the state detection program. FIG. 13 is a flow chart of a static state determination subroutine. FIG. 14 is a graph explaining thresholds Q and R for determining idle heating and the presence of a foreign liquid. Each step of the flow chart may be designated using an abbreviation "S".

Figure 9:
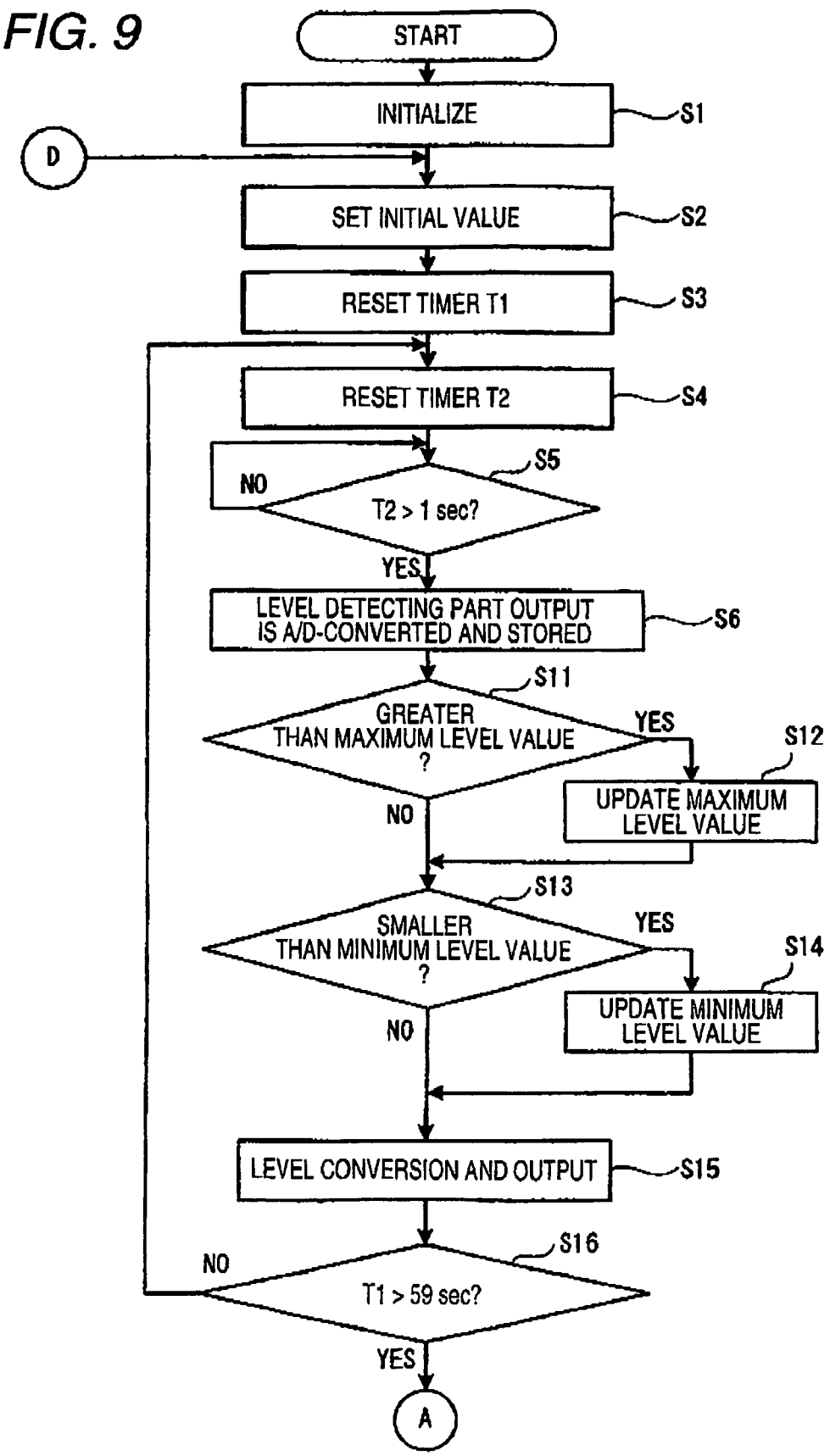
FIG. 9 is a flow chart of a main routine of a state detection program.

When the state of an aqueous urea solution is detected based on an instruction from an ECU, the state detection program stored in the ROM 222 is read into a predetermined storage area of the RAM 300 and executed. As shown in FIG. 9, initialization is first carried out (step S1) to reset all of parameters and count values in the storage areas of the RAM 300 shown in FIG. 4. Then, initial values are set (step S2), and initial values stored in the ROM 222 are written as the detection values, maximum and minimum level values in the level fluctuation storage areas 301, the voltage Vn in the voltage storage area 302, and the difference ΔVmn in the voltage difference storage area 303. For example, when the level of an aqueous urea solution under measurement can be A/D-converted into digital values representing liquid levels in 65536 steps, 0 and 65535 are stored as the maximum and minimum level values, respectively, in the level fluctuation storage areas 301.

The timer T1 is then reset (step S3), and reference is made to a count value in a timer program (not shown) which is separately executed to store the value in a timer count value storage area 306 as the initial value of the timer Ti. Similarly, the timer T2 is set (step S4), and a count value in the timer program is stored in a timer count value storage area 306 as the initial value of the timer T2.

There is a lapse time of 1 sec after the timer T2 is reset at step S5 (S5: NO). At this point in the process, reference is made to a count value in the timer program to check whether 1 sec has passed or not. This determination is based on whether or not the difference between the count value and the initial value of the timer T2 stored at step S4 is greater than a value corresponding to 1 sec. If 1 sec has passed (S5: YES), an output from the level detecting part 70 is A/D-converted through the level detection circuit unit 250 and input to the microcomputer 220. The input value is stored in a level fluctuation storage area 301 of the RAM 300 as a detection value of the level of the aqueous urea solution, based on the above-described principle of level detection (step S6).

At step S11, the level detection value stored in the level fluctuation storage area 301 is compared with the maximum level value in the level fluctuation storage area 301. If the detection value is greater than the maximum level value (S11: YES), the detection value is stored to update the maximum level value (step S12), and the process proceeds to step S13. The process also proceeds to step S13 when the detection value is equal or smaller than the maximum level value (S11: NO), and the level detection value is compared with the minimum level value just as done at step S11. If the detection value is equal to or greater than the minimum level value, the minimum level value is not updated. If the detection value is smaller than the minimum level value (S13: YES), the detection value is stored as the minimum level value. The minimum level value is thus updated (step S14), and the process proceeds to step S15.

At step S15, the level detection value stored in the level fluctuation storage area 301 at step S6 is converted into an output value representing the actual level of the aqueous urea solution using a conversion formula or table which is experimentally generated and stored in the ROM 222 in advance. The converted level value is output to the ECU from the liquid state detecting sensor 100 (step S15).

The process then checks whether or not 59 sec have elapsed after timer T1 has been reset at step S3 (step S16). If not, the process returns to step S4 (S16: NO) to repeat steps S4 to S15. If 59 sec have passed after timer T1 has been reset (S16: YES), the process proceeds to step S21 shown in FIG. 10. The CPU 221 which repeats the processes at steps S4 to S15 to update the maximum and minimum level values of the aqueous urea solution and to store these values in the level fluctuation storage areas 301 corresponds to the "level signal storage unit" of the invention.

Figure 10:
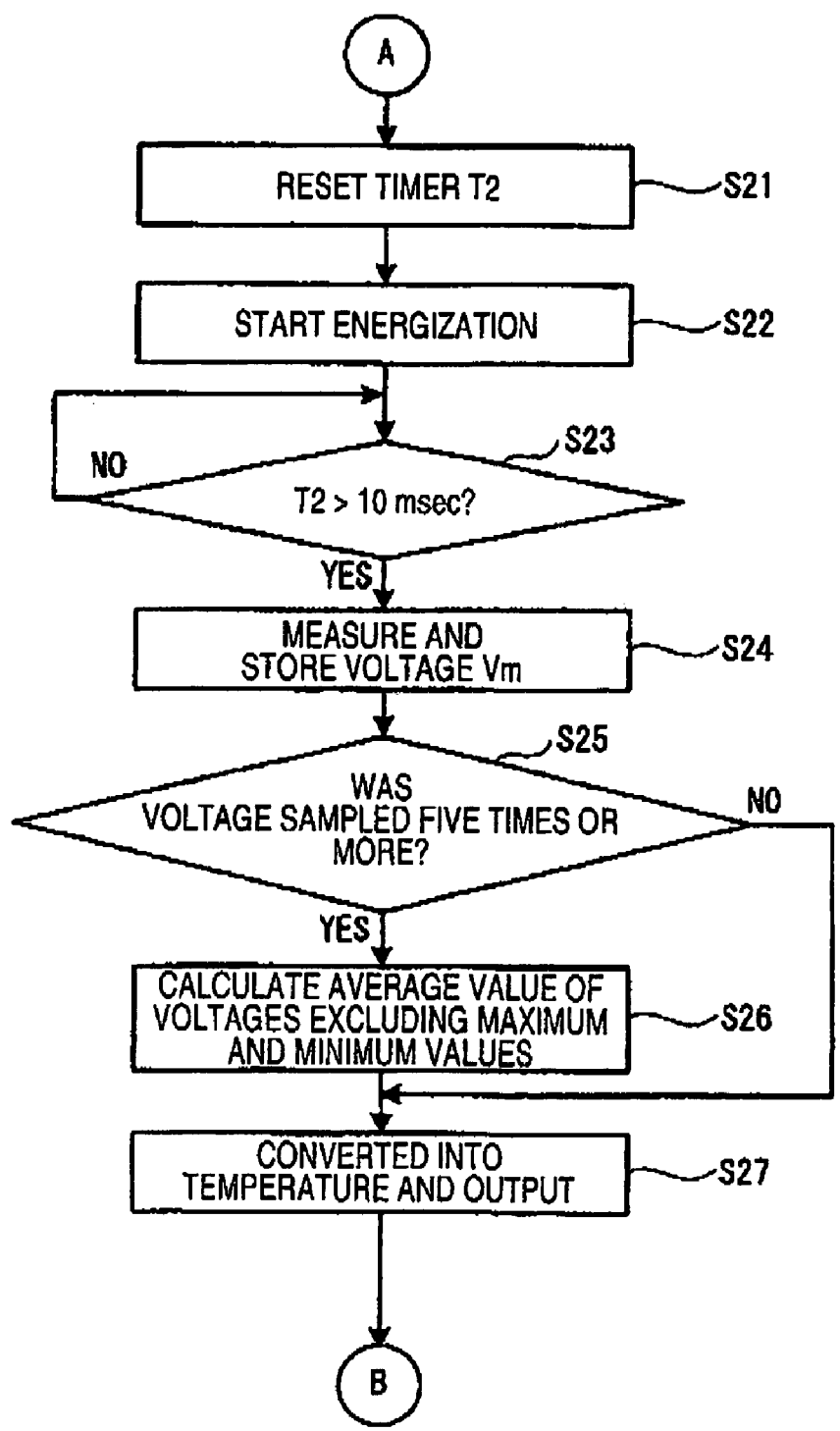
FIG. 10 is the flow chart of the main routine of the state detection program.

As shown in FIG. 10, at step S21, the timer T2 is reset just as done at step S4 (step S21), and the count value of the timer program at that time is stored as the initial value of the timer T2. Then, a control signal is transmitted from the microcomputer 220 to the switch 260, whereby the switch 260 is closed to cause the constant current output part 240 to start energizing the heating resistor 114 (step S22). As described above, a current stabilization time of 10 msec is set after the start of energization of the heating resistor 114. At the next step S23, the process checks whether or not 10 msec have passed after the timer T2 has been reset at step S21, and the process stands by if not (S23: NO). When a standby time of 10 msec has passed (S23: YES), a voltage detected by the heating resistor 114 is measured by the differential amplifier circuit unit 230, and the detection voltage is input to the microcomputer 220 and stored in a voltage storage area 302 as the voltage Vm (step S24).

The storage areas for the voltage Vm among the voltage storage areas 302 are referred to at the next step S25 to check whether five or more voltages have been stored or whether the measurement of the detection voltage at step S24 has been performed five times or more (step S25). If the voltage has been sampled less than five times (S25: NO), the process directly proceeds to step S27 to convert the voltage Vm into a temperature as described below.

On the other hand, at the fifth or later cycle of step S25, five voltages are stored in the storage areas for the voltage Vm among the voltage fluctuation storage areas 302. It is therefore determined that the sampling has been performed five times or more (S25: YES), and the process proceeds to step S26. Since the most recent five voltages among the detection voltages thus measured are stored in the storage areas for the voltage Vm as described above, the earliest voltage among them is overwritten at the sixth or later cycle of step S24 of the state detection program. Then, step 26 calculates an average value of three voltages among the five most recent voltages stored in the storage areas for the voltage Vm among the voltage storage areas 302 excluding the maximum and minimum values (S26).

At step S27, a calculation is carried out based on Expressions 1 and 2 by substituting the average voltage Vm calculated at step S26 for $V_T$ when the process at step S26 has been performed, and substituting the most recent voltage stored in the storage areas for the voltage Vm among the voltage storage areas 302 for $V_T$ when the process at step S26 has not been performed. Thus, the temperature T of the aqueous urea solution around the heating resistor 114 is obtained. The calculated temperature is transmitted from the input/output circuit unit 290 to the ECU as a temperature information signal (S27).

Figure 11:
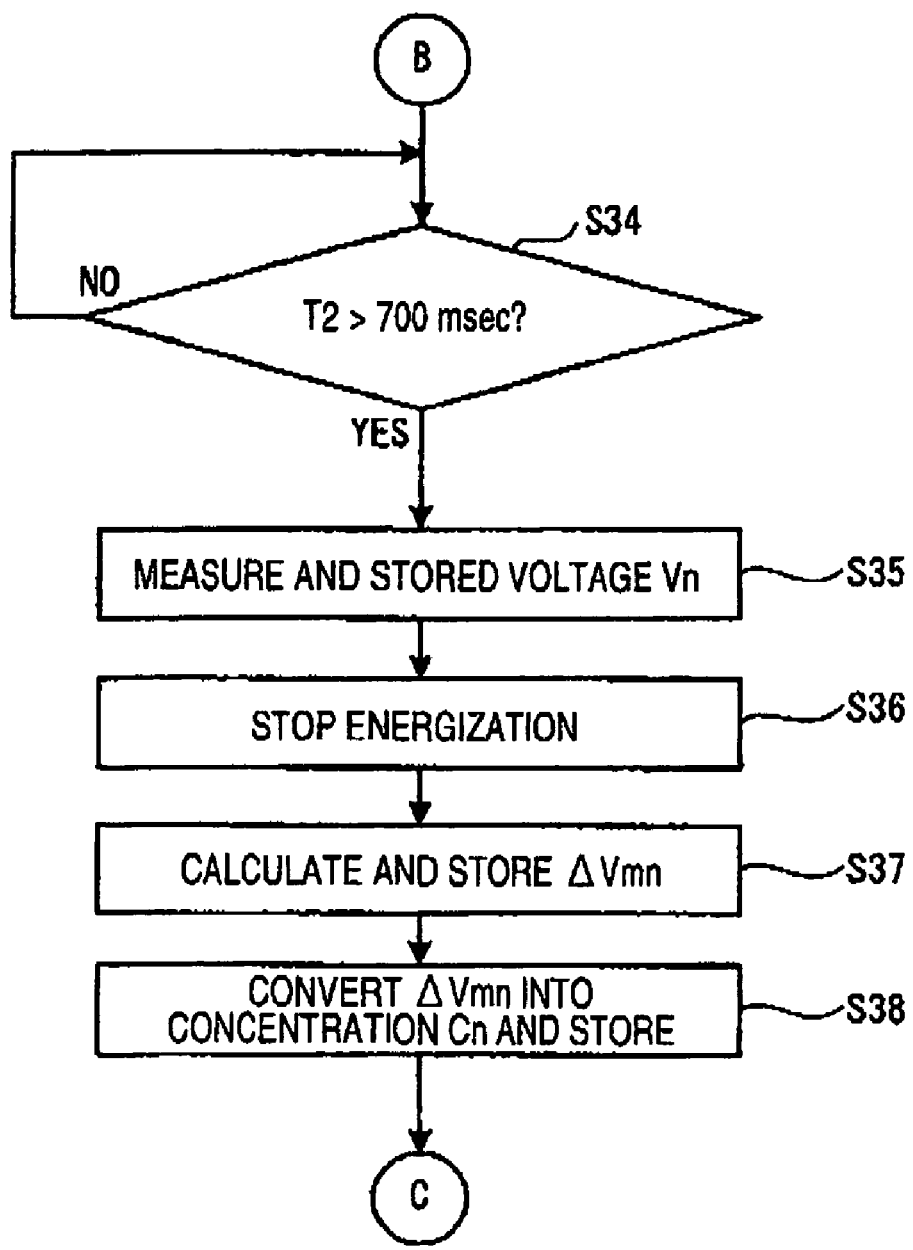
FIG. 11 is the flow chart of the main routine of the state detection program.

Next, the process at step S34 shown in FIG. 11 checks whether or not 700 msec have passed after timer T2 has been reset at step S21 (S34). If not, the process stands by (S34: NO). If 700 msec have elapsed (S34: YES), a voltage detected by the heating resistor 114 is measured in the same way as described above and stored in a voltage storage area 302 as the voltage Vn (step S35). When the voltage measurement is terminated, a control signal for the switch 260 is output from the microcomputer 220 to stop energization of the heating resistor 114 (step S36). Then, the difference between the voltage Vn and the most recent value of the voltage Vm stored at step S24 is calculated and stored in the voltage difference storage area 303 as the difference ΔVmn (step S37).

Conversion into concentration is carried out based on the above-described principle of urea concentration detection using the difference ΔVmn thus calculated. Specifically, a calculation based on Expressions 3 to 5 is carried out on the difference ΔVmn using the temperature T of the aqueous urea solution obtained at step S27 to obtain a converted value Cn of the concentration of urea contained in the aqueous urea solution. The converted concentration Cn is stored in the converted concentration storage area 305 (step S38). The CPU 221 which calculates the converted concentration Cn at step S38 based on the value ΔVmn calculated at step S37 corresponds to the "concentration detecting unit" of the invention.

Figure 12:
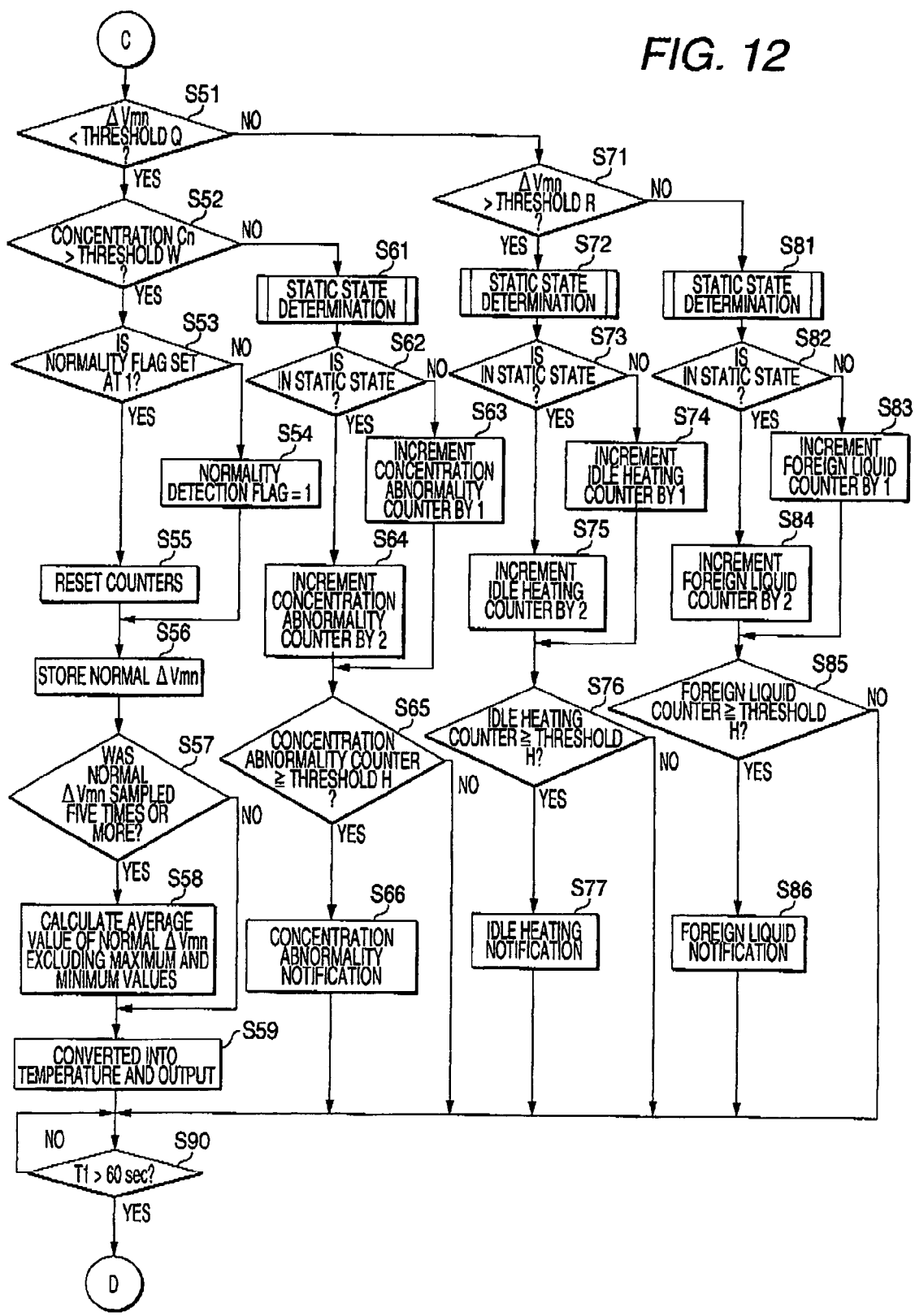
FIG. 12 is the flow chart of the main routine of the state detection program.

Determination processes at steps S51, S52, and S71 shown in FIG. 12 are then performed to determine whether or not the state of the aqueous urea solution thus detected is abnormal. The CPU 221 which determines the aqueous urea solution is in an abnormal state or not by performing the determination processes at steps S51, S52, and S71 corresponds to the "abnormality detection unit" of the invention.

First, at step S51, a comparison is made between the difference ΔVmn stored in the voltage difference storage area 303 and a maximum value of the voltage change ΔV (the threshold Q shown in FIG. 14 by way of example) based on values that the urea concentration of the aqueous urea solution can assume, the maximum value being experimentally determined and stored in the ROM 222 in advance (step S51). The process proceeds to step S71 if the difference ΔVmn is equal to or greater than the threshold Q (S51: NO).

At step S71, a comparison is made between the difference ΔVmn and a minimum value that a voltage change can assume when the heating resistor 114 is surrounded by air (the threshold R shown in FIG. 14 by way of example), the minimum value being experimentally determined and stored in the ROM 222 in advance (S71). If the difference ΔVmn is greater than the threshold R (S71: YES), the urea-water tank 98 is determined to be empty or in a state of idle heating, and the processes at steps S72 to S77 are performed. In this case, for example, the difference ΔVmn has a value of magnitude G that is greater than the threshold R as shown in FIG. 14 by way of example.

At step S72, a static state determination subroutine is executed as shown in FIG. 13 (S72). First, a normality detection flag in a flag storage area 307 is set at 0 (step S101), and a level fluctuation width (i.e., distribution range) is then calculated (step S102). This process calculates the difference between the maximum level value and the minimum level value stored in the level fluctuation storage areas 301 as the level fluctuation width. A comparison is made between the level fluctuation width and a maximum value (threshold J) of the level fluctuation width that the aqueous urea solution can assume when the aqueous urea solution can be regarded as being in a static state, the minimum value being experimentally determined and stored in the ROM 222 in advance (step S103). At this time, if the level fluctuation width is greater than the threshold J (S103: YES), it is determined that the aqueous urea solution is not in a static state, and a static state flag in a flag storage area 307 is set at 0 (step S111). When the level fluctuation width is equal to or smaller than the threshold J (S103: NO), it is determined that the aqueous urea solution is in a static state, and the static state flag in the flag storage area 307 is set at 1 (step S112). The process then returns to the main routine. The CPU 221 which executes the static state determination subroutine to determine whether the aqueous urea solution is in a static state or not corresponds to the "static state determination unit" of the invention.

When the process returns to the main routine of the state detection program shown in FIG. 12, a determination is made at step S73 whether or not the solution is in a static state. If the solution is determined to be in a static state from the static state flag set at 1 (S73: YES), an idle heating counter in a counter value storage area is incremented by 2 (step S75). If the solution is determined not to be in a static state from the static state flag set at 0 (S73: NO), idle heating counter is incremented by 1 (step 74). The process thereafter proceeds to step S76 at which reference is made to the value in the idle heating counter. If the value is smaller than a threshold H as an upper limit count value which is set and stored in the ROM 222 in advance (the threshold corresponds to the "abnormality determination value" of the invention and is set at 10, for example), the process directly proceeds to step S90 (S76: NO). Then, the process stands by for a lapse of 60 sec after the reset of the timer T1 at step S3 (S90: NO). When 60 sec has passed (S90: YES), the process returns to step S2. The CPU 221 which performs the processes at steps S74 and S75 and steps S63, S64, S83, and S84 to be described later to increment the count values in the idle heating counter, concentration abnormality counter, and foreign liquid counter corresponds to the "counter unit" of the invention. Further, the CPU 221 which performs determination processes at step S73 and steps S62 and S82 to be described later so as to set the count value incremented in each of the counters at different values depending on whether or not the aqueous urea solution is in a static state corresponds to the "set value changing unit" of the invention.

The idle heating counter is incremented as the main routine of the state detection program is repeatedly executed. When the value is equal to or exceeds the threshold H (S76: YES), a state of idle heating is determined to have occurred, and a notification signal notifying the ECU of the idle heating is transmitted via the input/output circuit unit 290 (step S77). Thereafter, the process returns to step S2 via step S90 as described above. The CPU 221 which performs determination processes at step S76 and steps S65 and S85 to be described later to determine the occurrence of a state of idle heating, a state regarded as a concentration abnormality, or a state in which container includes a foreign liquid corresponds to the "abnormality determination unit" of the invention. The CPU 221 which performs processes at step S77 and steps S66 and S86 to be described later to transmit a signal notifying the ECU of the state of idle heating, the state regarded as a concentration abnormality, or the inclusion of a foreign liquid corresponds to the "notification unit" of the invention.

When the difference $\Delta V_{mn}$ is a value equal to or smaller than the threshold R at the above-described step S71 (S71: NO), the liquid surrounding the heating resistor 114 is detected as being a liquid other than an aqueous urea solution (e.g., gas oil), and the processes at steps S81 to S86 are performed. In this case, for example, the difference $\Delta V_{mn}$ has a value having magnitude F which is in the range between the threshold Q and the threshold R, inclusive, as shown in FIG. 14 by way of example.

The static state determination subroutine described with reference to FIG. 13 is executed at step S81 to set the static state flag at 1 or 0 (S81). Similarly, the liquid is determined to be in a static state or not at step S82. If in a static state (S82: YES), the foreign liquid counter in the counter value storage area is incremented by 2 (step S84). If not in a static state (S82: NO), the foreign liquid counter is incremented by 1 (step S83). The process thereafter proceeds to step S85 at which reference is made to the value in the foreign liquid counter, and the process directly proceeds to step S90 if the value is smaller than the above-described threshold H (S85: NO). If the value in the foreign liquid counter is equal or greater than the threshold H (S85: YES), a foreign liquid is determined to be included in the aqueous urea solution tank 98, and a notification signal notifying the presence of a foreign liquid is transmitted to the ECU through the input/output circuit unit 290 (step S86). Thereafter, the process returns to step S2 via step S90 as described above.

When the difference $\Delta V_{mn}$ is smaller than the threshold Q at the above-described step S51 (S51: YES), the process proceeds to step S52. In this case, for example, the difference $\Delta V_{mn}$ has a value of magnitude E that is smaller than the threshold Q as shown in FIG. 14 by way of example.

At step S52, a comparison is made between the most recent converted concentration Cn stored in the converted concentration storage area 305 at step S38 and a maximum value of concentration that the liquid around the heating resistor 114 can assume when it is water (a threshold W which is not shown), the maximum value being experimentally determined and stored in the ROM 222 in advance (step S52). If the converted concentration Cn is equal to or smaller than the threshold W (S52: NO), an abnormality is detected as having occurred in the urea concentration of the aqueous urea solution contained in the urea-water tank 98, and processes at steps S61 to S66 are performed.

At step S61, the static state determination subroutine described with reference to FIG. 13 is executed, and the static state flag is set at 1 or 0 (step S61). Similarly, at step S62, a determination is made as to whether or not the liquid is in a static state. If in a static state (S62: YES), the concentration abnormality counter is incremented by 2 (S64). If the liquid is not in a static state (S62: NO), the concentration abnormality counter is incremented by 1 (S63). The process thereafter proceeds to step S65 at which reference is made to the value in the concentration abnormality counter, and the process directly proceeds to step S90 if the value is smaller than the above-described threshold H (S65: NO). If the value in the concentration counter is equal or greater than the threshold H (S65: YES), the process determines that there is an abnormality in the concentration of urea in the aqueous urea solution (e.g., a state in which excess water is included in the urea-water tank 98), and a notification signal notifying the ECU of the abnormality of concentration is transmitted via the input/output circuit unit 290 (step S66). Thereafter, the process returns to step S2 via step S90 as described above.

When the converted concentration Cn is greater than the threshold W at the above-described step S52 (S52: YES), the process determines that the aqueous urea solution contained in the urea-water tank 98 is not in any particular abnormal state, or in none of an empty state, a state in which the solution includes a foreign liquid, and a state in which the urea concentration is regarded as being abnormal. At this time, the normality detection flag is checked (step S53). If this determination process is performed for the first time, since the normality detection flag is 0 (S53: NO), the process proceeds to step S56 with the normality detection flag set at 1 (step S54).

If the aqueous urea solution is determined to be in a particular abnormal state (S51: NO or S51: YES and S52: NO), the normality detection flag is set at 0 at step S101 of the static state determination subroutine in FIG. 13. Therefore, when the process determines that the aqueous urea solution is not in a particular abnormal state twice or a greater number of times during repeated execution of the main routing of the state detection program (S51: YES and S52: YES), a "1" will have been stored at the normality detection flag at the process of step S54 previously performed. In this case, each of the concentration abnormality counter, idle heating counter, and foreign liquid counter stored in the counter value storage areas 308 is reset (step S55).

The process then determines that urea in the aqueous urea solution has a normal concentration, and the difference $\Delta V_{mn}$ is stored in a normal voltage difference storage area 304 (step S56). At the next step S57, reference is made to the normal voltage difference storage areas 304 for storing the difference $\Delta V_{mn}$ to determine whether the number of voltage differences stored is five or whether the storage of a normal difference $\Delta V_{mn}$ at step S56 has been performed five times or more (S57). If the number of times the sampling of the difference $\Delta V_{mn}$ has been performed is less than five (S57:

NO), the process directly proceeds to step S59, and the difference ΔVmn is converted into a concentration.

At step S56, the five most recent normal values of the difference ΔVmn are stored in the storage areas for the difference ΔVmn as described above. When the process determines that urea in the aqueous urea solution has a normal concentration six times or more during repeated execution of the state detection program, the oldest voltage difference is overwritten.

On the contrary, if the number of voltage differences stored is five or more, the process determines that a normal difference ΔVmn has been sampled five times or more (S57: YES), and a process is performed to calculate an average value of three voltage differences which are the five most recent differences ΔVmn in the normal voltage difference storage areas 304 excluding the maximum and minimum values (step S58).

At step S59, conversion into concentration is performed similarly to step S38 based on the above-described principle of urea concentration detection. This is done by substituting the average value of the difference ΔVmn calculated at step S58 for ΔV when the process at step S58 has been performed, and by substituting the most recent difference stored in the normal voltage difference storage areas 304 for storing the difference ΔVmn for ΔV when the process at step S58 has not been performed. That is, a converted concentration of urea included in the aqueous urea solution is obtained by performing a calculation using Expressions 3 to 5 on the normal difference ΔVmn using the temperature T of the aqueous urea solution obtained at step S27. The converted urea concentration thus calculated is transmitted from the input/output circuit unit 290 to the ECU as a concentration information signal (step S59). Thereafter, the process returns to step S2 via step S90 to repeat the state detection program.

It should further be apparent to those skilled in the art that various changes in form and detail of the invention as shown and described above may be made. It is intended that such changes be included within the spirit and scope of the claims appended thereto. For example, according to the state detection program, the temperature of an aqueous urea solution is calculated based on Expressions 1 and 2 at step S27, and the concentration of urea is calculated based on Expressions 3 to 5 at steps S38 and S59. Such values may alternatively be obtained at steps S27, S38, and S59 by referring to values in respective tables which are experimentally created and stored in predetermined storage areas of the ROM 222 in advance.

The standby time at each of steps S5, S16, S23, S34, and S90 is merely an example, and an optimum standby time may alternatively be set through experimentation. While the threshold H of the concentration abnormality counter, idle heating counter, and foreign liquid counter is set at 10 by way of example in the present embodiment, an optimum threshold may alternatively be set through experimentation. While the counters are incremented by 2 in a static state and incremented by 1 in a non-static state in the above description, the increments may alternatively be set at optimum values (an optimum ratio between them) through experimentation. Both of the threshold and the counter increments may be changed to allow a more accurate determination of an abnormal state.

An alternative arrangement may be employed in which abnormality of the concentration of an aqueous urea solution is determined in the same way as the present embodiment when the aqueous urea solution is in a static state, and in which the abnormality determination itself is not performed when the solution is not in a static state. A specific example of this arrangement is to directly proceed to step S90 when the process at any of steps S62, S73, and S82 results in a negative determination. As thus described, the accuracy of determination of an abnormal state can be improved by skipping the abnormality determination itself when there is a possibility of an erroneous determination of an abnormal state.

At steps S51 and S71, the difference ΔVmn is compared with the thresholds Q and R to determine a state of idle heating or the inclusion of a foreign liquid. The converted concentration Cn calculated at steep S38 may alternatively be compared with a threshold. Similarly, the difference ΔVmn may alternatively be compared with a threshold to determine whether or not urea in the aqueous urea solution has a normal concentration.

Figure 15:
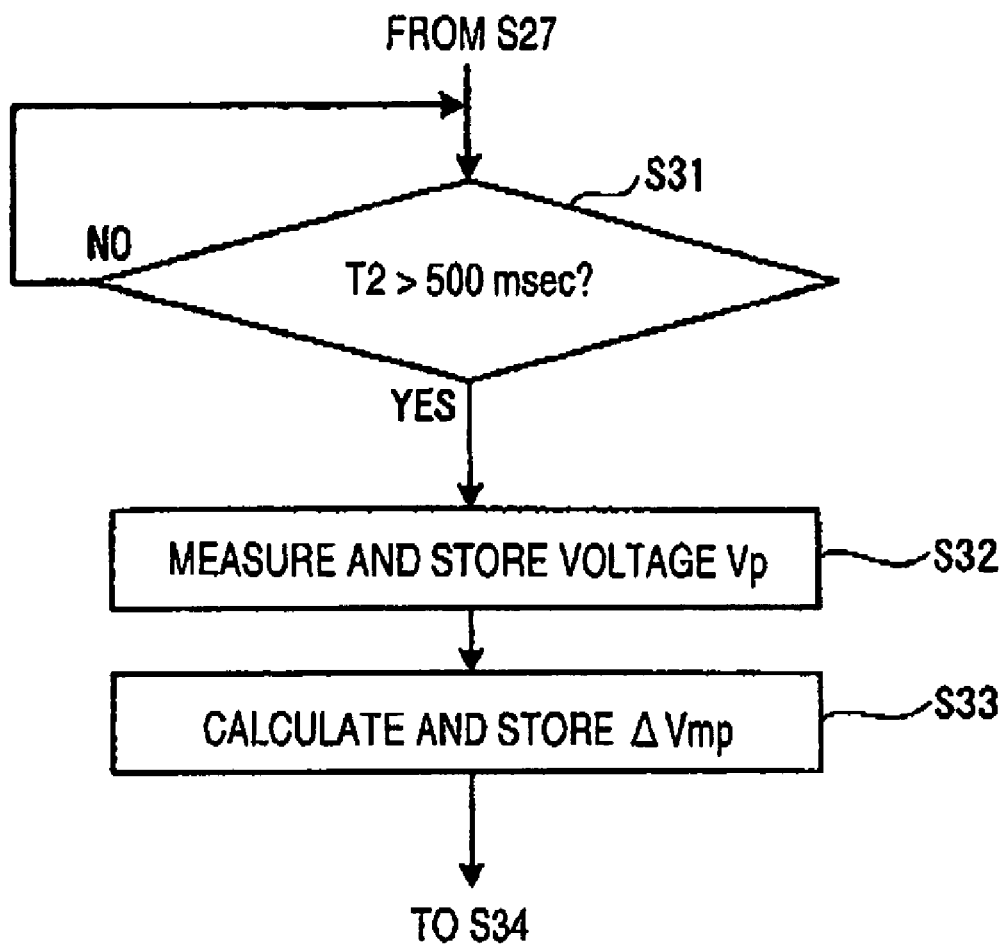
FIG. 15 is a flow chart showing a series of processes added to the main routine as a modification of the state detection program.
Figure 16:
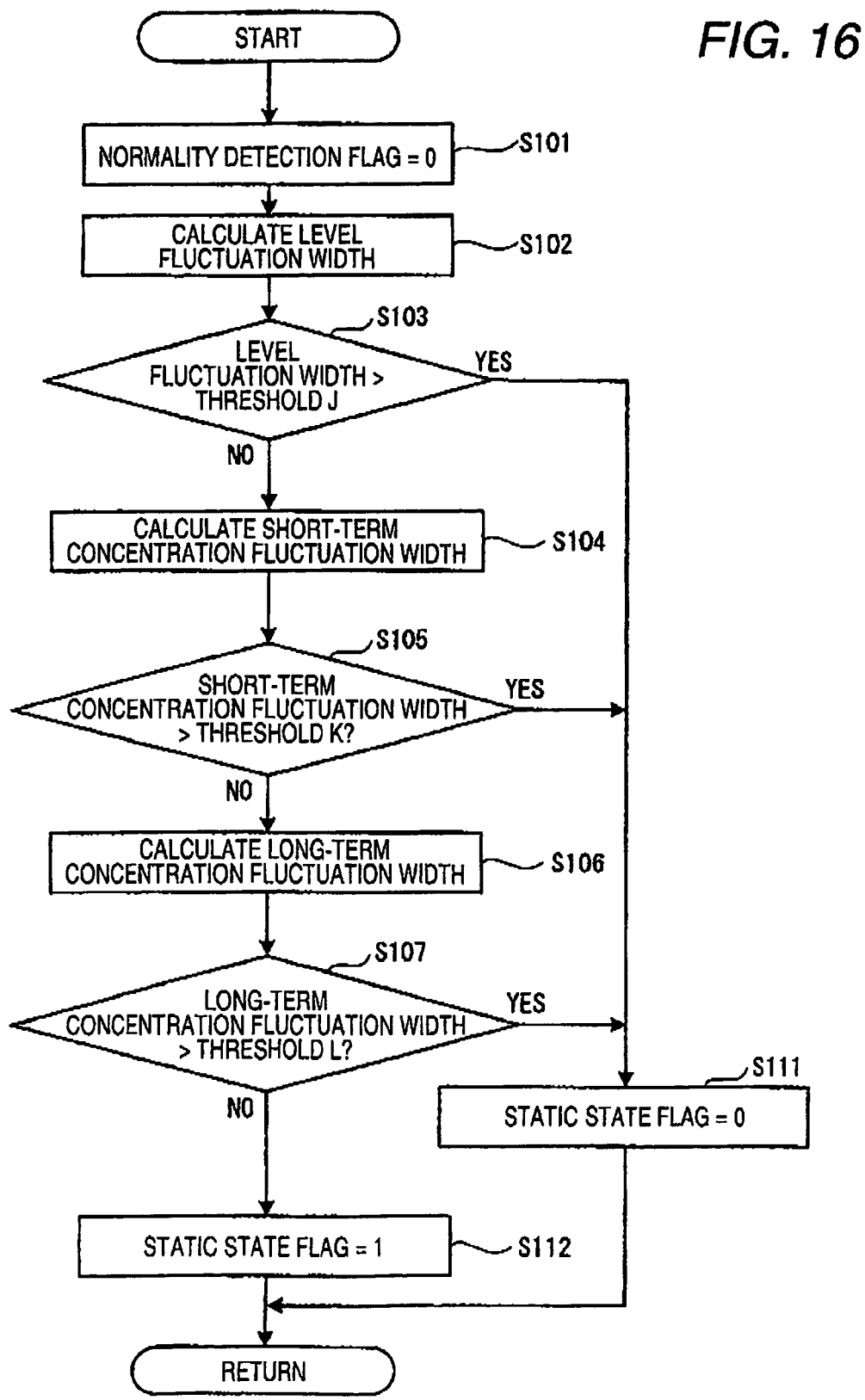
FIG. 16 is a flow chart showing a modification of the static state determination program.

In the static state determination subroutine, a determination is made as to whether or not an aqueous urea solution is in a static state based on a level fluctuation width that is a difference between a maximum value and a minimum value of the level of the aqueous urea solution repeatedly detected at steps S4 to S16. Alternatively, a determination may be made based on the width of fluctuation of the urea concentration of the aqueous urea solution. FIGS. 15 and 16 show an example of such a determination method. FIG. 15 is a flow chart showing a series of processes added to the main routine as a modification of the state detection program. FIG. 16 is a flow chart showing a modification of the static state determination subroutine. Processes having the same contents as those of the static state determination subroutine of the present embodiment are indicated by like step numbers.

Although not shown, the voltage storage areas 302 of the RAM 300 include a storage area for a voltage Vp, and the voltage difference storage areas 303 include a storage area for a difference ΔVmp. The converted concentration storage area 305 includes a storage area for a converted concentration Cp. Two storage areas are provided for the converted concentration Cn. Furthermore, the two most recent converted concentrations Cn are stored with converted concentrations calculated prior to discarding the same. The two most recent converted concentrations Cn are used to determine a static state based on a long-term concentration fluctuation width in the modification of the static state determination subroutine shown in FIG. 16 which will be described later.

The series of processes shown in FIG. 15 is used to determine a static state based on a short-term concentration fluctuation width in the modification of the static state determination subroutine shown in FIG. 16 which is inserted between,step S27 (see FIG. 10) and step S34 (see FIG. 11) of the state detection program and which will be described later. As shown in FIG. 15, the process checks at step S31 whether or not 500 msec have passed after the timer T2 has been reset at step S21 in FIG. 10 (S31), and the process stands by until the time has passed (S31: NO). When 500 msec has elapsed (S31: YES), a voltage detected by the heating resistor 114 is measured in the same way as the present embodiment and stored in a voltage storage area 302 as the voltage Vp (step S32). The difference between the voltage Vp and the most recent value of the voltage Vm stored at step S24 is calculated and stored in the storage area for the difference ΔVmp among the voltage difference storage areas 303 (step S33), and the process proceeds to step S34 in FIG. 11. The series of processes allows the urea concentration to be sampled at timing slightly earlier (200 mscc earlier, in this modification) than the timing at which the liquid state detecting sensor 100 detects the urea concentration of the aqueous urea solution.

At step S38 in FIG. 11, the converted concentration Cn is obtained using the difference ΔVmn as described, and the converted concentration Cp is further obtained using the difference ΔVmp and stored in the storage area for the converted concentration Cp among the converted concentration storage areas 305.

In the modification of the static state determination subroutine shown in FIG. 16, when the level fluctuation width is equal to or smaller than the threshold J at step S103 (S103: NO), static state determination is performed using a short-term concentration fluctuation width at steps S104 and S105 and using a long-term concentration fluctuation width at steps 106 and S107 instead of setting the static state flag immediately at 1.

First, a short-term concentration fluctuation width is calculate at step S104 (S104). At this step, the difference between the converted concentrations Cn and Cp stored in the converted concentration storage areas 305 is obtained. That is, the width of concentration fluctuation during a short period between the point 500 msec after the start of energization of the heating resistor and the point 700 msec after the same is obtained as a difference. The difference (short-term concentration fluctuation width) is compared with a maximum value that the fluctuation width of the urea concentration of the aqueous urea solution can assume when the aqueous urea solution is in a static state in the short period (a threshold K), the maximum value being experimentally determined and stored in the ROM 222 in advance (S105). At this time, if the short-term concentration fluctuation width is greater than the threshold K (S105: YES), the process determines that the aqueous urea solution is not in a static state, and the static state flag is set at 0 (step S111).

If the short-term concentration fluctuation width is equal to or smaller than the threshold K (S105: NO), a calculation is further carried out to obtain a long-term concentration fluctuation width (step S106). This process obtains the difference between the previous value and the latest value of the converted concentration Cn stored in the converted concentration storage areas 305. That is, a width of concentration fluctuation is obtained as a difference between the most recent urea concentration of the aqueous urea solution and the urea concentration detected 600 msec before the same. The difference (long-term concentration fluctuation width) is compared with a maximum value that the fluctuation width of the urea concentration of the aqueous urea solution can assume when the aqueous urea solution is in a static state in the longer period (a threshold L), the maximum value being experimentally determined and stored in the ROM 222 in advance (S107). At this time, if the long-term concentration fluctuation width is greater than the threshold L (S107: YES), the process determines that the aqueous urea solution is not in a static state, and the static state flag is set at 0 (step S111). If the long term concentration fluctuation width is equal to or smaller than the threshold L (S107: NO), the process determines that the aqueous urea solution is in a static state, and the static state flag is set at 1 (step S112). Then, the process may return to the main routine.

While the above-described modification of the static state determination subroutine represents an example in which the determination is made based on a level fluctuation width, based on a short-term concentration fluctuation width, and based on a long-term concentration fluctuation width in the order listed, the order of determination may be arbitrarily changed.

The circuit board 60 may be provided as a circuit board for buffering the output of the level detecting part 70 and the liquid property detecting part 30. The circuit board may be connected to an external circuit carrying the microcomputer 220 and the like to perform level detection and to detect temperature and concentration under control of the external circuit While sampling is performed five times at steps S25 and S57 to obtain voltages Vm and normal differences ΔVmn to be averaged, the invention is not limited to sampling five times. The process of excluding maximum and minimum values may be deleted from the processes of obtaining those averages.

The invention can be applied to liquid state detecting sensors capable of detecting the level and concentration of a liquid.

This application is based on Japanese Patent Application JP 2005-328198, filed Nov. 11, 2005, the entire content of which is hereby incorporated by reference, the same as if set forth at length.

What is claimed is:

1. A liquid state detecting apparatus comprising:
   a detecting element provided in a liquid container which outputs a signal associated with a concentration of a particular component of a liquid contained in the liquid container;
   a first abnormality detecting unit which determines whether or not the liquid is in a particular abnormal state based on the output signal of the detecting element,
   a level detecting part which outputs a signal according to a level of the liquid contained in the liquid container; and
   a static state determination unit which determines whether or not the liquid in the liquid container is in a static state based on the output signal of the level detecting part,
   wherein the determination made by the static state determination unit is reflected in the determination made by the first abnormality detecting unit.

2. The liquid state detecting apparatus as claimed in claim 1, comprising a level signal storing unit which acquires the signal from the level detecting part twice or a greater number of times within a predetermined period and in which at least a maximum value and a minimum value of the signals from the level detecting part within the predetermined period are stored, wherein the static state determination unit determines that the liquid is not in the static state when a level difference that is a difference between the maximum value and the minimum value of the signals from the level detecting part stored in the level signal storage unit is greater than a reference level difference serving as a reference for determining the static state.

3. The liquid state detecting apparatus as claimed in claim 1, wherein:
   the level detecting part includes a first electrode and a second electrode extending in a longitudinal direction of the level detecting part to form a capacitor whose electrostatic capacity changes according to the level of the liquid contained in the liquid container between the first electrode and the second electrode; and
   the detecting element is integrated with the level detecting part in an insulated state with a part of the detecting element located beyond a tip of the level detecting part.

4. The liquid state detecting apparatus as claimed in claim 1, further comprising a notification unit which notifies an external circuit that the liquid is in the particular abnormal state when so determined by the first abnormality detecting unit.

5. The liquid state detecting apparatus as claimed in claim 1, wherein the particular abnormal state of the liquid is a state in which the liquid is not present in the liquid container, a state in which a foreign liquid is included in the liquid container, or a state in which the concentration of the particular component included in the liquid is regarded as being abnormal.

6. The liquid state detecting apparatus as claimed in claim 1, wherein the liquid is an aqueous urea solution and the particular component is urea.

7. The liquid state detecting apparatus as claimed in claim 1, comprising:
- a second abnormality detecting unit which detects whether or not the liquid is in a particular abnormal state based on the output signal of the detecting element and a threshold set in association with the particular abnormal state;
- a counter unit which increments an abnormality determination value by a predetermined count value each time the second abnormality detecting unit determines that the liquid is in the particular abnormal state; and
- a set value changing unit which sets at least one of the predetermined count value and an abnormality determination value serving as a reference for the determination made by the first abnormality detecting unit to a first value when the static state determination unit determines that the liquid is in the static state, and to a different value when the liquid is not in the static state, wherein:
- the first abnormality detecting unit determines that the liquid is in the particular abnormal state when the abnormality count value incremented by the counter unit reaches the abnormality determination value; and
- the determination by the static state determination unit is reflected in the determination made by the first abnormality detecting unit by the change in the setting of at least one of the predetermined count value and the abnormality determination value made by the set value changing unit.

8. The liquid state detecting apparatus as claimed in claim 7, wherein:
- the detecting element includes a heating resistor which generates heat when energized and a concentration detecting unit which obtains a value of a difference between a first corresponding value corresponding to a first resistance of the heating resistor acquired after energization of the heating resistor is started and a second corresponding value corresponding to a second resistance acquired after the heating resistor is energized for a certain period of time and which detects a concentration of a particular component included in the liquid associated with the difference; and
- the second abnormality detecting unit compares at least one of the difference and the concentration with the threshold set in association with the particular abnormal state of the liquid to detect whether or not the liquid is in the particular abnormal state.

* * * * *